US011445672B2

(12) United States Patent
Van Zee

(10) Patent No.: US 11,445,672 B2
(45) Date of Patent: Sep. 20, 2022

(54) LETTUCE VARIETY NUN 09093 LTL

(71) Applicant: NUNHEMS B.V., Nunhem (NL)

(72) Inventor: Johan Van Zee, s-Gravenzande (NL)

(73) Assignee: NUNHEMS B.V., Nunhem (NL)

( * ) Notice: Subject to any disclaimer, the term of this patent is extended or adjusted under 35 U.S.C. 154(b) by 26 days.

(21) Appl. No.: 16/944,989

(22) Filed: Jul. 31, 2020

(65) Prior Publication Data

US 2020/0396933 A1 Dec. 24, 2020

Related U.S. Application Data

(60) Provisional application No. 62/882,320, filed on Aug. 2, 2019.

(51) Int. Cl.
*A01H 5/10* (2018.01)
*A01H 6/14* (2018.01)

(52) U.S. Cl.
CPC ............. *A01H 6/1472* (2018.05); *A01H 5/10* (2013.01)

(58) Field of Classification Search
CPC ................. A01H 5/12; A01H 6/1472
See application file for complete search history.

(56) References Cited

U.S. PATENT DOCUMENTS

| 8,237,019 | B2 | 8/2012 | Van Den Ackerveken et al. |
| 8,809,634 | B1 * | 8/2014 | Roca ........................ A01H 5/12 800/305 |
| 2008/0222949 | A1 | 9/2008 | Bissonnette et al. |
| 2015/0126380 | A1 | 5/2015 | Van Dun |
| 2015/0245570 | A1 | 9/2015 | Vogelaar et al. |

FOREIGN PATENT DOCUMENTS

| EP | 1197137 A1 | 4/2002 |
| WO | 2008092505 A1 | 8/2008 |
| WO | 2017144669 A1 | 8/2017 |

OTHER PUBLICATIONS

"DUS Test for Lettuce—*Lactuca sativa* L.", Calibration Manual, Harmonized with Naktuinbow and NCSS(/NARO), Comply with UPOV TG/13/10, Dec. 26, 2016, pp. 1-56.
"Guidelines for the Handling of a Dispute on Essential Derivation in Lettuce", International seed Federation, May 2004, pp. 1-3.
"Lettuce-UPOV Code(s): LACTU_SAT(*Lactuca sativa* L.)," Guidelines for the Conduct of Tests for Distinctness, Uniformity and Stability, UPOV, International Union for the Protection of New Varieties of Plants, Geneva, TG/13/11, Jun. 14, 2019, pp. 1-50.
"Objective description of variety Lettuce (*Lactuca sativa* L.)", US Department of Agriculture, Agricultural Marketing Service, Science and Technology, Plant Variety Protection Office, USDA, Exhibit C, Dec. 2018, pp. 1-21.
Bertier, et al., "High-Resolution Analysis of the Efficiency, Heritability, and Editing Outcomes of CRISPR/Cas9-Induced Modifications of NCED4 in Lettuce (*Lactuca sativa*)", G3: Genes, Genomes, Genetics, vol. 8, Issue 5, May 1, 2018, pp. 1513-1521.
Brotman, et al., "Resistance gene homologues in melon are linked to genetic loci conferring disease and pest resistance", Theoretical and Applied Genetics, vol. 104, May 2002, pp. 1055-1063.
Gonai, et al., "Abscisic acid in the thermoinhibition of lettuce seed germination and enhancement of its catabolism by gibberellin", Journal of Experimental Botany, vol. 55, Issue 394, Jan. 1, 2004, pp. 111-118.
Hunter, et al., "Oxidative discolouration in whole-head and cut lettuce: biochemical and environmental influences on a complex phenotype and potential breeding strategies to improve shelf-life", Euphytica, vol. 213, Article No. 180, Jul. 18, 2017, pp. 1-16.
Needleman, et al., "A general method applicable to the search for similarities in the amino acid sequence of two proteins", Journal of Molecular Biology, vol. 48, Issue 3, 1970, pp. 443-453.
Nikolova, et al., "Diploidization of cucumber (*Cucumis sativus* L.) haploids by colchicine treatment", Acta Societas Botanicorum Poloniae, vol. 65, Issue 3-4, 1996, pp. 311-317.
Rice, et al., "EMBOSS: The European Molecular Biology Open Software Suite", Trends in Genetics, vol. 16, Issue 6, Jun. 1, 2000, pp. 276-277.
Robert W. Allard, "Principles of Plant Breeding", Second edition, 1999, pp. 64-67.
Smith, et al., "Leaf Lettuce Production in California", University of California Agricultural and Natural Resources, Publication 7216, 2011, pp. 1-6.
Songstad, et al., "Genome Editing of Plants", Critical Reviews in Plant Sciences, vol. 36, Issue 1, 2017, pp. 1-23.
Teng, et al., "Rapid Regeneration of Lettuce from Suspension Culture", HortScience, vol. 27, Issue 9, Sep. 1992, pp. 1030-1032.
Teng, et al., "Regenerating Lettuce from Suspension Culture in a 2-Liter Bioreactor", HortScience, vol. 26, Issue 6, Jun. 1993, pp. 669-671.
Turini, et al., "Iceberg Lettuce Production in California," University of California Agricultural and Natural Resources, Publication 7215, Sep. 1, 2011, pp. 1-6.
Vos, et al., "AFLP: a new technique for DNA fingerprinting", Nucleic Acids Research, vol. 23, Issue 21, Nov. 11, 1995, pp. 4407-4414.
Wijnker, et al., "Hybrid recreation by reverse breeding in *Arabidopsis thaliana*", Nature Protocols, vol. 9, Issue 4, Mar. 6, 2014, pp. 761-772.
Xinrun, et al., "Genotypic effects on tissue culture response of lettuce cotyledons", Journal of Genetics and Breeding, vol. 46, Issue 3, 1992, pp. 287-290.

* cited by examiner

*Primary Examiner* — Weihua Fan
(74) *Attorney, Agent, or Firm* — ArentFox Schiff LLP

(57) ABSTRACT

The disclosure relates to lettuce variety NUN 09093 LTL as well as seeds and plants and heads or leaves thereof. Lettuce variety NUN 09093 LTL is a baby leaf lettuce variety, comprising resistance to Downy Mildew (*Bremia lactucae*) Isolates Bl:16-33EU, *Nasonovia ribisnigri* Biotype Nr:0, and *Fusarium oxysporum* f. sp. *lactucae* Race 1 IR.

35 Claims, 7 Drawing Sheets

LETTUCE VARIETY NUN 09093 LTL

CROSS REFERENCE TO RELATED APPLICATION

This application claims priority to U.S. Provisional Application No. 62/882,320, filed on Aug. 2, 2019, which is hereby incorporated by reference in its entirety.

FIELD OF THE DISCLOSURE

The disclosure relates to the field of plant breeding and, more specifically, to the development of lettuce variety NUN 09093 LTL. The disclosure further relates to vegetative reproductions of lettuce variety NUN 09093 LTL, methods for tissue culture of lettuce variety NUN 09093 LTL, and to phenotypic variants of lettuce variety NUN 09093 LTL. The disclosure also relates to progeny of lettuce variety NUN 09093 LTL and the hybrid varieties obtained by crossing lettuce variety NUN 09093 LTL as a parent line with plants of other varieties or parent lines.

BACKGROUND OF THE DISCLOSURE

The goal of vegetable breeding is to combine various desirable traits in a single variety. Such desirable traits may include greater yield, resistance to diseases, insects or other pests, tolerance to heat and drought, better agronomic quality, higher nutritional value, enhanced growth rate, and improved shelf life.

The development of commercial lettuce cultivars or varieties requires the crossing of lettuce plants, and the evaluation of the crosses. Pedigree breeding and recurrent selection are examples of breeding methods used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the inbred lines or hybrids from these crosses are evaluated to determine which have commercial potential.

All cultivated forms of lettuce belong to the highly polymorphic species *Lactuca sativa* that is grown for its edible head and leaves. *Lactuca sativa* is in the Asteraceae (Compositae) family. Lettuce is related to chicory, sunflower, aster, dandelion, artichoke, and chrysanthemum. *L. sativa* is one of about 300 species in the genus *Lactuca*. There are many types of lettuce, and new types are constantly in development. Types of lettuce include Cutting/Leaf, Iceberg/Crisphead, Cos or Romaine, Batavian, Salinas Group, Latin, Butterhead, Great Lakes Group, Eastern (Ithaca) Group, Bibb, Vanguard Group, Multileaf, or Stem lettuce. Lettuce is typically consumed fresh and occasionally as a cooked vegetable. It is popularly used in salads, wraps, and sandwiches.

Fresh lettuce is available in the United States year-round although the greatest supply is from May through October. For planting purposes, the lettuce season is typically divided into three categories, early, mid and late, with the coastal areas planting from January to August, and the desert regions planting from August to December. California and Arizona are the two largest producers of lettuce in the United States.

Changes in lifestyle primarily due to increasing health awareness results to growing demand for healthy convenience food. Supermarkets, restaurants, catering firms, and convenience stores are constantly looking for more colorful garnishing for sandwiches, wraps, and ready-to-eat snacks such as salads. The changing food and consumer trends present opportunities for breeding companies to develop new varieties with specific shapes of leaves, specific average size of leaves, prominent color, glossiness, taste, and a wide variety of texture. Other breeding objectives include disease or pest resistance, yield, prolonged shelf life, and suitability to climatic requirements.

SUMMARY OF VARIOUS ASPECTS OF THE DISCLOSURE

The disclosure provides for lettuce variety NUN 09093 LTL, products thereof, and methods of using the same. NUN 09093 LTL is a leaf lettuce variety of the Frillice type and is suitable for growing in the open field.

In another aspect, the plant of lettuce variety NUN 09093 LTL, or part thereof, or progeny thereof comprises resistance to Downy Mildew (*Bremia lactucae*) Isolates Bl:16-33EU, *Nasonovia ribisnigri* Biotype Nr:0, and *Fusarium oxysporum* f. sp. *lactucae* Race 1 IR, measured according to UPOV standards described in TG/13/11.

The disclosure also provides a lettuce plant or part thereof having all of the physiological and morphological characteristics of lettuce variety NUN 09093 LTL, when grown under the same environmental conditions. The disclosure also provides for a progeny of lettuce variety NUN 09093 LTL. In another aspect, the disclosure provides a plant or a progeny retaining all or all but one, two, or three of the "distinguishing characteristics" of the plant of lettuce variety NUN 09093 LTL, or all but one, two, or three of the "morphological and physiological characteristics" of the plant of lettuce variety NUN 09093 LTL and methods of producing that plant or progeny.

In one aspect, the plant or progeny has all or all but one, two, or three of the physiological and morphological characteristics of the plant of lettuce variety NUN 09093 LTL, when grown under the same environmental conditions and e.g., evaluated at significance levels of 1%, 5%, or 10% significance (which can be expressed as a p-value) for quantitative characteristics and identical (same degree or type) for non-quantitative characteristics, wherein a representative sample of seed of variety NUN 09093 LTL has been deposited under Accession Number NCIMB 43767. In another aspect, the plant or progeny has all or all but one, two, or three of the physiological and morphological characteristics as listed in Tables 1-2 of the plant of lettuce variety NUN 09093 LTL, when measured under the same environmental conditions and e.g., evaluated at significance levels of 1%, 5%, or 10% significance (which can also be expressed as a p value) for quantitative characteristics and identical (same degree or type) for non-quantitative characteristics.

In another aspect, the plant of lettuce variety NUN 09093 LTL, or part thereof, or a progeny thereof has 21, 22, more or all of the following distinguishing characteristics when compared to Reference Variety as shown in Table 3: 1) white seed color; 2) fewer leaves; 3) smaller plant spread of frame leaves; 4) shorter plant height; 5) lighter plant weight; 6) smaller plant diameter; 7) longer fourth leaf length; 8) smaller fourth leaf width; 9) dentate fourth leaf apical margin; 10) moderate yellow green fourth leaf color; 11) more leaf divisions; 12) concave shape at longitudinal section of mature leaf; 13) greyish green mature leaf color; 14) less undulation of mature leaf margin; 15) deeper incision of mature leaf margin; 16) deeper secondary margin of mature leaf; 17) flabellate mature leaf venation; 18)

shorter mature leaf width; 19) smaller mature leaf width; 20) smaller mature leaf size; 21) shorter height from base of head to apex (core length); and 22) thinner diameter at base of head (core width), when grown under the same environmental conditions.

In another aspect, the disclosure provides a seed of lettuce variety NUN 09093 LTL, wherein a representative sample of said seed has been deposited under Accession Number NCIMB 43767. The disclosure also provides for a plurality of seeds of lettuce variety NUN 09093 LTL. The lettuce seed of variety NUN 09093 LTL may be provided as an essentially homogeneous population of lettuce seed. The population of seed of lettuce variety NUN 09093 LTL may be particularly defined as an essentially free from other seed. The seed population may be grown into plants to provide an essentially homogeneous population of lettuce plants described herein.

The disclosure also provides a plant grown from a seed of lettuce variety NUN 09093 LTL and a plant part thereof.

The disclosure further provides a lettuce head and/or a lettuce leaf produced on a plant grown from a seed of lettuce variety NUN 09093 LTL.

The disclosure furthermore provides a seed growing or grown on a plant of lettuce variety NUN 09093 LTL (e.g., produced after pollination of the flower of lettuce variety NUN 09093 LTL).

In another aspect, the disclosure provides for a plant part obtained from lettuce variety NUN 09093 LTL, wherein said plant part is: a leaf, a part of a leaf, a head, a part of a head, a fruit, a part of a fruit, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, a cotyledon, a pistil, an anther, or a flower or a part thereof. Heads and leaves are particularly important plant parts. Such plant parts may be suitable for sexual reproduction, vegetative reproduction, or a tissue culture. In another aspect, the plant part obtained from variety NUN 09093 LTL is a cell, optionally a cell in a cell or tissue culture. That cell may be grown into a plant of lettuce variety NUN 09093 LTL.

In another aspect, the disclosure provides for an inbred variety of NUN 09093 LTL.

In another aspect, the disclosure provides for a hybrid lettuce variety NUN 09093 LTL.

In another aspect, the disclosure provides a cell culture of lettuce variety NUN 09093 LTL and a plant regenerated from lettuce variety NUN 09093 LTL, wherein the plant has all of the physiological and morphological characteristics of lettuce variety NUN 09093 LTL when grown under the same environmental conditions, as well as methods for culturing and regenerating lettuce variety NUN 09093 LTL. Alternatively, a regenerated plant may have one characteristic that is different from lettuce variety NUN 09093 LTL and which otherwise has all the physiological and morphological characteristics of lettuce variety NUN 09093 LTL.

The disclosure also provides a vegetatively propagated plant of variety NUN 09093 LTL having all or all but one, two, or three of the morphological and physiological characteristics of lettuce variety NUN 09093 LTL when grown under the same environmental conditions as well as methods for vegetatively propagating lettuce variety NUN 09093 LTL.

In another aspect, the disclosure provides a method of producing a lettuce plant comprising crossing lettuce variety NUN 09093 LTL with itself or another lettuce variety and selecting a progeny lettuce plant from said crossing or selfing.

The disclosure also provides a method of producing a lettuce plant derived from lettuce variety NUN 09093 LTL.

In further aspect, the disclosure provides a method of producing hybrid lettuce seed comprising crossing a first parent lettuce plant with a second parent lettuce plant and harvesting the resultant hybrid lettuce seed, wherein said first parent lettuce plant or second parent lettuce plant is lettuce variety NUN 09093 LTL. Also provided is a hybrid lettuce seed produced from crossing a first parent lettuce plant with a second parent lettuce plant and harvesting the resultant hybrid lettuce seed, wherein said first parent lettuce plant or second parent lettuce plant is lettuce variety NUN 09093 LTL. Moreover, a hybrid lettuce plant grown from the hybrid lettuce seed is provided.

In another aspect, the disclosure provides a method of introducing a single locus conversion into the plant of variety NUN 09093 LTL, wherein a representative sample of seed of said lettuce variety has been deposited under Accession Number NCIMB 43767, and wherein the single locus converted plant comprises the single locus conversion and otherwise all of the physiological and morphological characteristics of lettuce variety NUN 09093 LTL.

In yet another aspect, the disclosure provides a method of introducing a desired trait into lettuce variety NUN 09093 LTL, said method comprises transforming the plant of variety NUN 09093 LTL with a transgene that confers the desired trait, wherein a representative sample of seed of said lettuce variety has been deposited under Accession Number NCIMB 43767, and wherein the transformed plant contains the desired trait and otherwise all of the physiological and morphological characteristics of lettuce variety NUN 09093 LTL.

The disclosure also provides a method of producing a modified lettuce plant with a desired trait, said method comprises mutating a lettuce plant or plant part of lettuce variety NUN 09093 LTL, wherein a representative sample of said seed has been deposited under Accession Number NCIMB 43767, and wherein the mutated plant contains the desired trait and otherwise all of the physiological and morphological characteristics of lettuce variety NUN 09093 LTL.

In one aspect, the single locus conversion or desired trait is yield, size, storage properties, color, taste, enhanced nutritional quality, post-harvest quality, male sterility, herbicide tolerance, insect resistance, pest resistance, disease resistance, environmental stress tolerance, modified carbohydrate metabolism, or modified protein metabolism, or the mutation occurs in any of the following genes: Ferulate-5-hydroxylase, dmr1, dmr6, NCED4, PAL, PPO.

In another aspect, the disclosure provides a container comprising the plant, plant part, or seed of lettuce variety NUN 09093 LTL.

Also provided is a food, a feed, or a processed product comprising the plant part of lettuce variety NUN 09093 LTL, wherein the plant part is a leaf or part thereof.

DEFINITIONS

Figure 1:
FIG. 1 shows the mature plant of lettuce variety NUN 09093 LTL.
Figure 2:
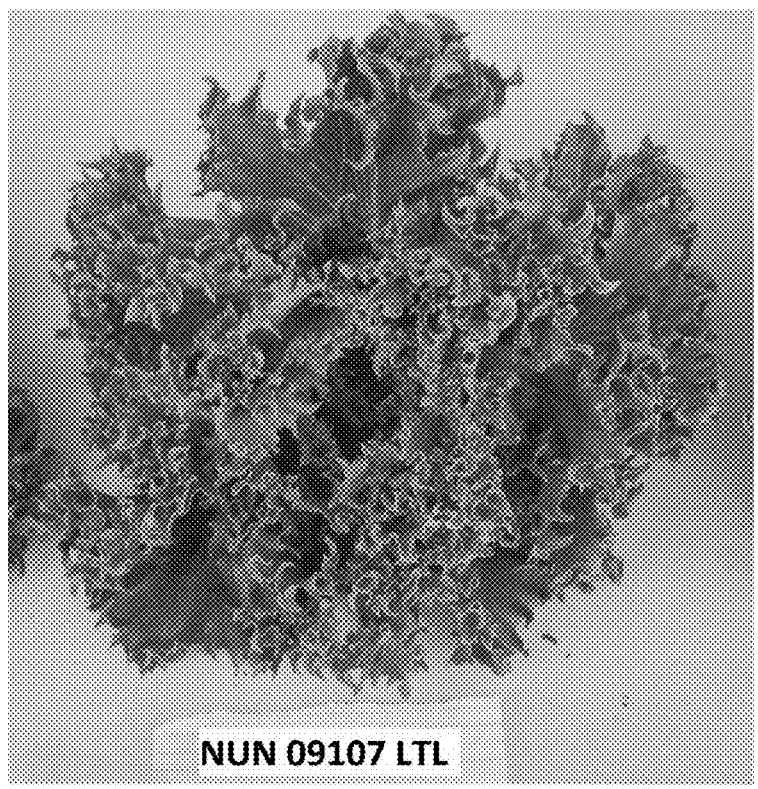
FIG. 2 shows the mature plant of the Reference Variety.
Figure 3:
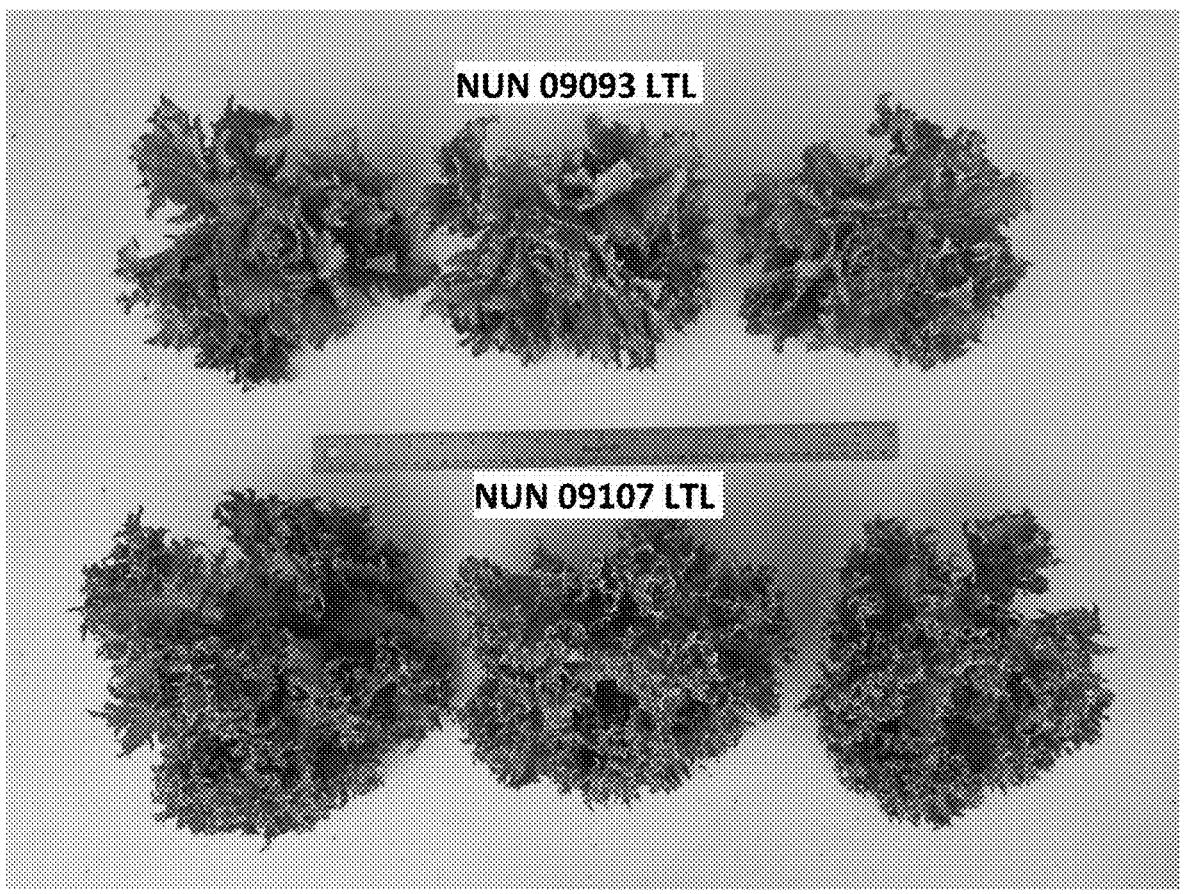
FIG. 3 shows the comparison of mature plants of lettuce variety NUN 09093 LTL and the Reference Variety.
Figure 4:
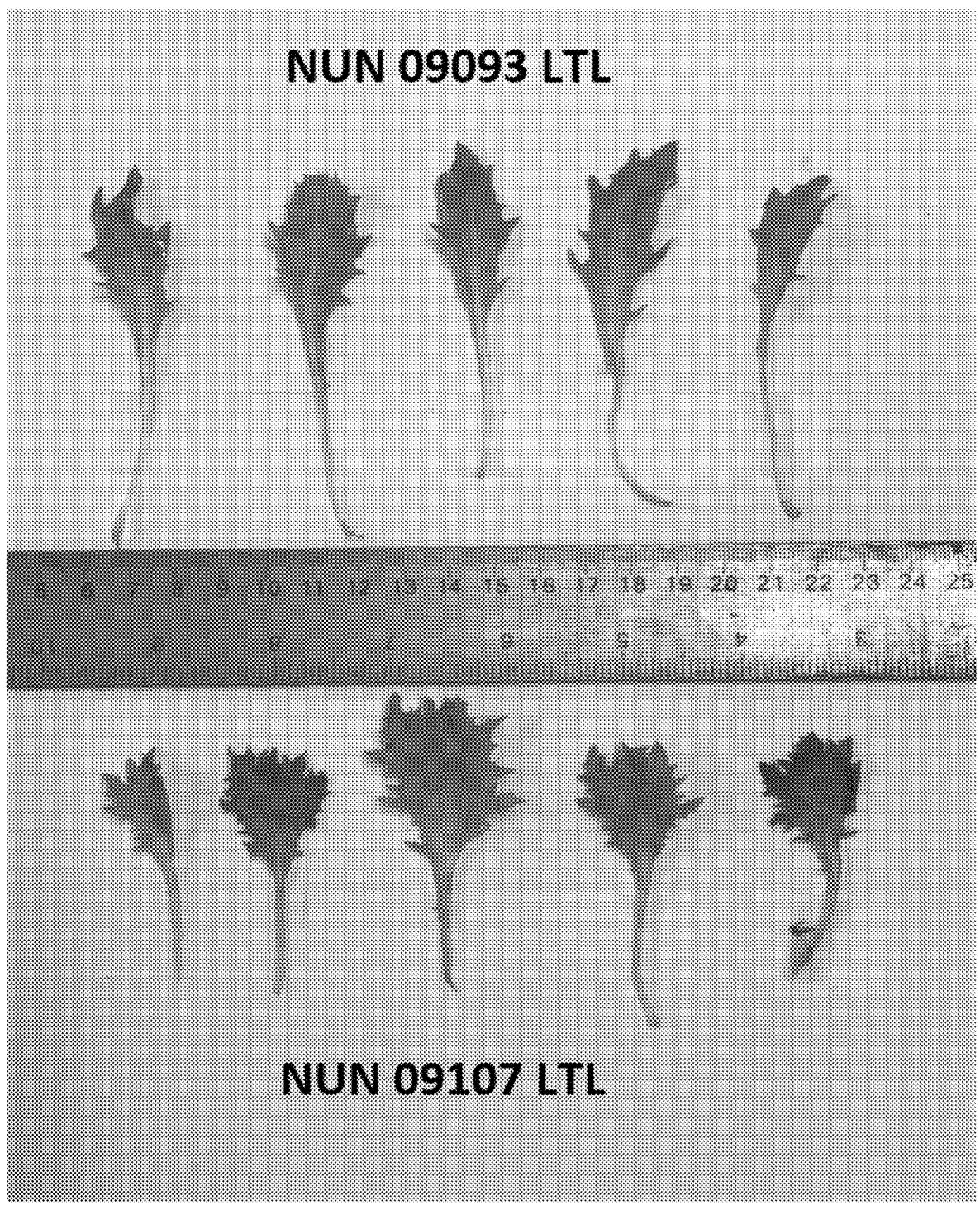
FIG. 4 shows the comparison of fourth leaves of lettuce variety NUN 09093 LTL and the Reference Variety.
Figure 5:
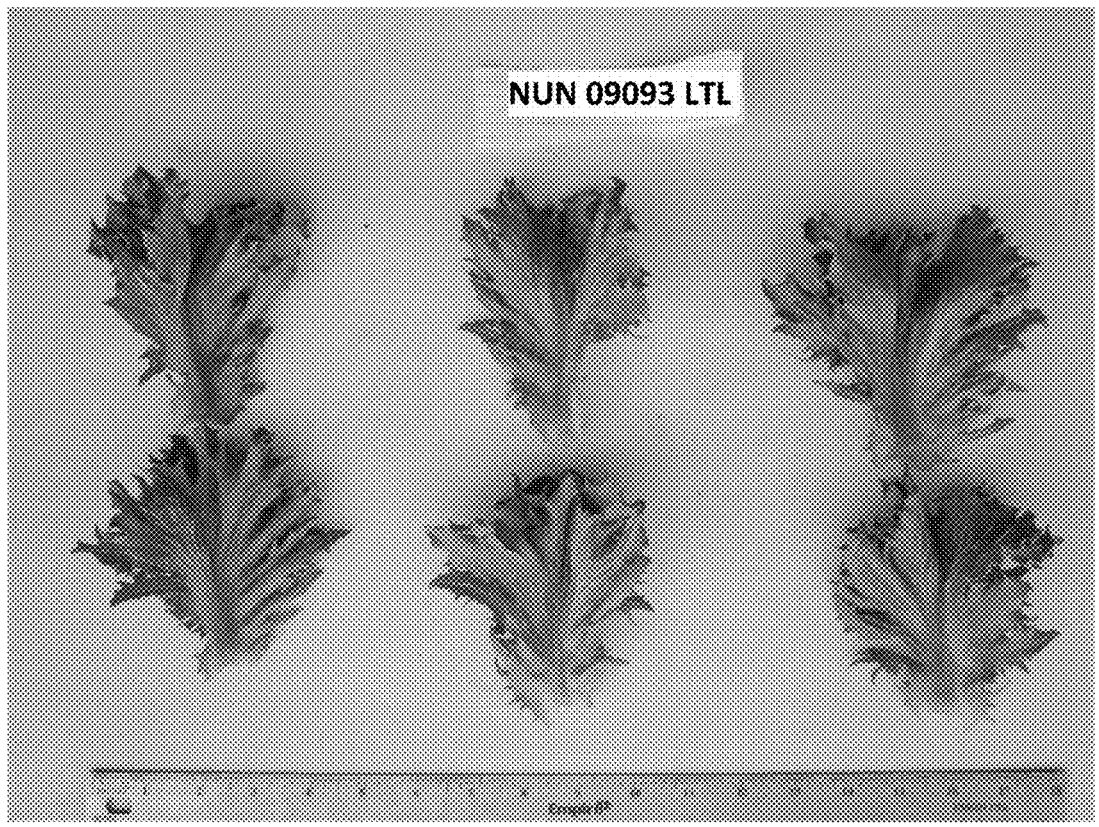
FIG. 5 shows the mature leaves of lettuce variety NUN 09093 LTL.
Figure 6:
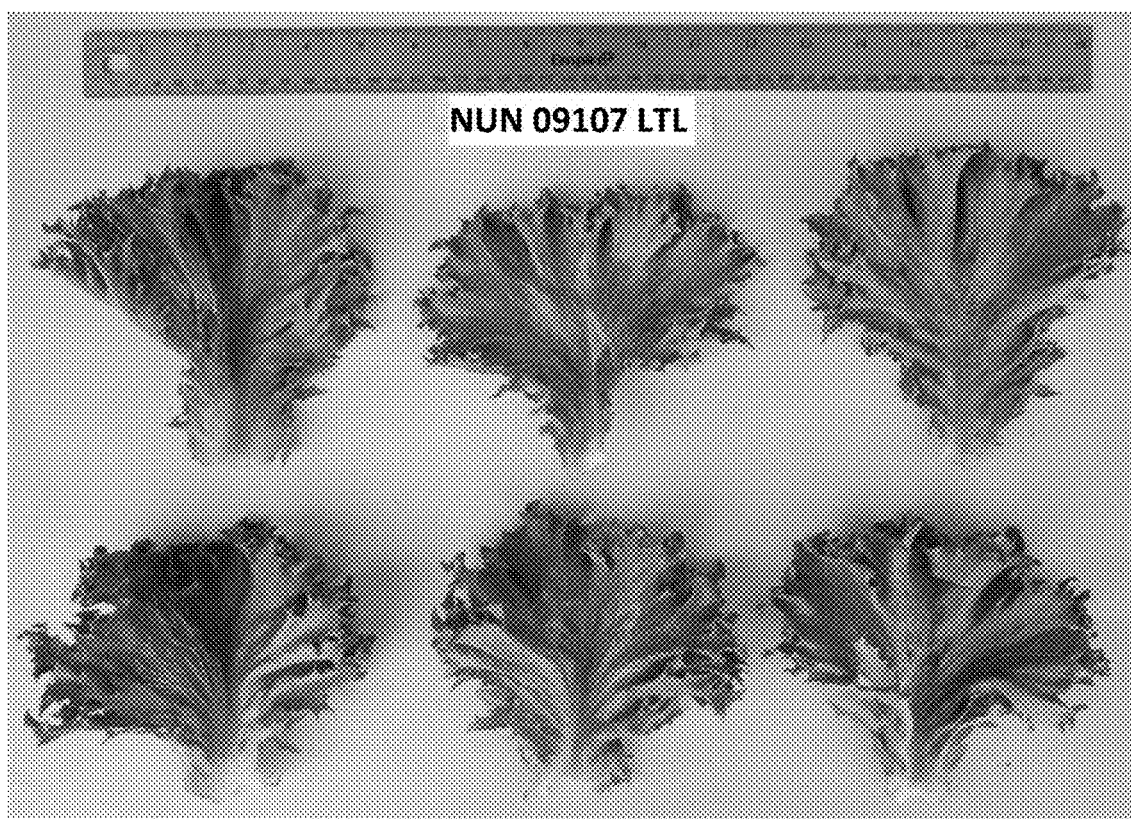
FIG. 6 shows the mature leaves of the Reference Variety.
Figure 7:
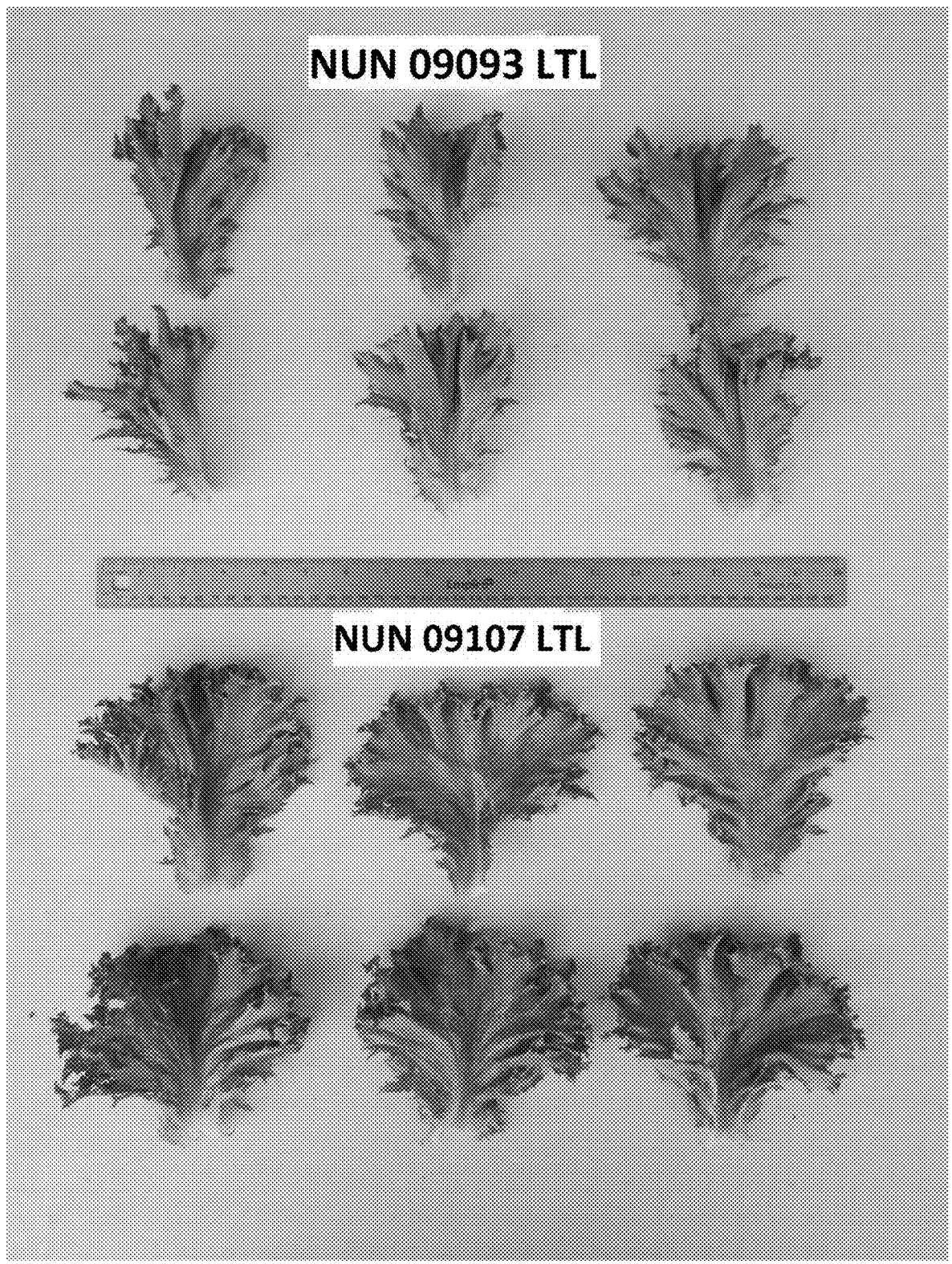
FIG. 7 shows the comparison of mature leaves of lettuce variety NUN 09093 LTL and the Reference Variety.
Figure 8:
FIG. 8 shows the core of lettuce variety NUN 09093 LTL.
Figure 9:
FIG. 9 shows the core of the Reference Variety.
Figure 10:
FIG. 10 shows the comparison of the cores of lettuce variety NUN 09093 LTL and the Reference Variety.

"Lettuce" refers herein to plants of the species *Lactuca sativa* L. The most commonly eaten parts of a lettuce plant are the head or a leaf. The head comprises a core and leaves, which may be divided in inner and outer leaves.

"Cultivated lettuce" refers to plants of *Lactuca sativa* (e.g., varieties, breeding lines or cultivars of the species *L. sativa* as well as crossbreds thereof, or crossbreds with other *Lactuca sativa* species, or even with other *Lactuca* species), cultivated by humans and having good agronomic characteristics.

"Leaf" lettuce refers to a type of lettuce having very loose leaves and does not form a head.

The terms "lettuce plant designated NUN 09093 LTL," "NUN 09093 LTL," "inbred NUN 09093," "09093 LTL," "lettuce 09093," or "Rockflash" are used interchangeably herein and refer to the lettuce plant of variety NUN 09093 LTL, representative sample of said seed has been deposited under Accession Number NCIMB 43767.

"Plant" includes the whole plant or any parts or derivatives thereof, preferably having the same genetic makeup as the plant from which it is obtained.

"Plant part" includes any part of a plant, such as a plant organ (e.g., harvested or non-harvested leaves), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, a hypocotyl, a cotyledon, a scion, a graft, a stock, a rootstock, a pistil, an anther, or a flower. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprises one or two sets of chromosomes derived from the parent plant (e.g., from lettuce variety NUN 09093 LTL). An F1 progeny produced from self-pollination of the inbred variety NUN 09093 LTL will thus comprise two sets of chromosomes derived from lettuce variety NUN 09093 LTL, while an F1 progeny derived from cross-fertilization of lettuce variety NUN 09093 LTL will comprise only one set of chromosomes from lettuce variety NUN 09093 LTL and the other set of chromosomes from the other parent.

A "seed of lettuce variety NUN 09093 LTL" refers to a lettuce seed which can be grown into a plant of lettuce variety NUN 09093 LTL, wherein a representative sample of viable seeds of lettuce variety NUN 09093 LTL has been deposited under Accession Number NCIMB 43767. A seed can be in any stage of maturity, for example, a mature, viable seed, or an immature non-viable seed. A seed comprises an embryo and maternal tissues.

An "embryo of lettuce variety NUN 09093 LTL" refers to an embryo as present in a seed of lettuce variety NUN 09093 LTL, a representative sample of said seed of lettuce variety NUN 09093 LTL having been deposited under Accession Number NCIMB 43767.

A "seed grown on lettuce variety NUN 09093 LTL" refers to a seed grown on a mature plant of variety NUN 09093 LTL. The "seed grown on lettuce variety NUN 09093 LTL" contains tissues and DNA of the maternal parent, lettuce variety NUN 09093 LTL. The "seed grown on lettuce variety NUN 09093 LTL" contains an F1 embryo. When said seed is planted, it grows into a first generation progeny plant of variety NUN 09093 LTL. Since lettuce variety NUN 09093 LTL is an inbred variety and thus highly homozygous, the set of chromosomes inherited by the first generation is predictable.

An "essentially homogeneous population of lettuce seed" is a population of seeds where at least 97%, 98%, 99% or more of the total population of seeds are seeds of lettuce variety NUN 09093 LTL.

An "essentially homogeneous population of lettuce plants" is a population of plants where at least 97%, 97%, 99% or more of the total population of plants are plants of lettuce variety NUN 09093 LTL.

The phrase "essentially free from other seed" refers to a population of seeds where less than 3%, 2%, 1%, or even less, of the total population of seed is seed that is not a lettuce seed or, in another option, less than 3%, 2%, 1%, or less, of the total population of seed is seed that is not a seed of lettuce variety NUN 09093 LTL.

"Cotyledon" refers to one of the first leaves of the embryo of a seed plant.

"Head" as used herein refers to lettuce heads, i.e., the plant without the root system, for example, substantially all harvested leaves. Encompassed are immature leaves (e.g., "baby leaf") and mature leaves.

The "base" of a plant is the part of a lettuce plant where the leaves are attached to the root system of the plant.

"Core length" of the internal lettuce stem is measured from the base of the cut and trimmed head to the tip of the stem.

"Core Length to Head Diameter Ratio (CLHD Ratio)" refers to the mean core length/head diameter ratio. It is calculated by dividing the mean core length with the mean head diameter. This is an indication of the head shape and of the ability of a lettuce plant to reduce the amount of surface which is on or close to the ground.

"Head weight" refers to the mean weight of saleable lettuce head, cut, and trimmed to market specifications.

"Head diameter" refers to the mean diameter of the cut and trimmed head, sliced vertically, and measured at the widest point perpendicular to the stem.

"Head height" refers to the mean height of the cut and trimmed head, sliced vertically, and measured from the base of the cut stem to the leaf tip.

"Harvested plant material" refers herein to plant parts (e.g., leaves or heads detached from the whole plant) which have been collected for further storage and/or further use.

"Harvested seeds" refers to seeds harvested from a line or variety, e.g., produced after self-fertilization or cross-fertilization and collected.

"First water date" refers to the date the seed first receives adequate moisture to germinate. This can and often does equal the planting date.

"Maturity date" refers to the stage when the plants are of full size or optimum weight, in marketable form or shape to be of commercial or economic value. This is also the time when measuring parameters of "mature" leaves.

"Yield" means the total weight of all lettuce heads or leaves harvested per hectare of a particular line or variety. It is understood that "yield" expressed as weight of all lettuce heads or leaves harvested per hectare can be obtained by multiplying the number of plants per hectare times the "yield per plant."

"Marketable yield" means the total weight of all marketable lettuce heads or leaves harvested per hectare of a particular line or variety, e.g., lettuce heads or leaves suitable for being sold for fresh consumption, having good color, glossiness size and texture and no or very low levels of deficiencies. A "marketable lettuce head or leaf" is a head or leaf that has commercial value.

"USDA descriptors" are the plant variety descriptors described for lettuce in the "Objective description of Variety—Lettuce (Lactuca sativa L.)," as published by U.S. Department of Agriculture, Agricultural Marketing Service, Science and Technology, Plant Variety Protection Office (June 2015, revised December 2018), and which can be downloaded from the world-wide web at ams.usda.gov/ under services/plant-variety-protection/pvpo-c-forms under lettuce. "Non-USDA descriptors" are other descriptors suitable for describing lettuce.

"UPOV descriptors" are the plant variety descriptors described for lettuce in the "Guidelines for the Conduct of Tests for Distinctness, Uniformity and Stability," TG/13/11 (Revised 2019 Jun. 14), as published by UPOV (International Union for the Protection of New Varieties and Plants) and which can be downloaded from the world-wide web at upov.int/ under edocs/tgdocs/en/tg013.pdf, which is hereby incorporated by reference in its entirety. Likewise, "UPOV methods" to determine specific parameters for the characterization of lettuce are described at upov.int.

"Calibration Manual: DUS Test for Lettuce" refers to the calibration book for lettuce which provides guidance for describing a lettuce variety, as published by Naktuinbow (Netherlands) and National Agriculture and Food Research Organization (NARO Japan) (Dec. 26, 2016) and based on the UPOV Guideline TG/13/10 Rev. 2

"RHS" or "RHS color" refers to the color chart of the Royal Horticultural Society (UK), which publishes a botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart 2007.

"Reference Variety" refers herein to variety NUN 09107 LTL, a variety from Nunhems B.V. with commercial name Danstar, which has been planted in a trial together with lettuce variety NUN 09093 LTL. The characteristics of lettuce variety NUN 09093 LTL were compared with the characteristics of the Reference Variety as shown in Tables 1 and 2. The distinguishing characteristics between lettuce variety NUN 09093 LTL and the Reference Variety are shown in Table 3.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the progenitor parent, the recurrent parent, the plant used for tissue- or cell culture, etc. A physiological or morphological characteristic can be a numerical characteristic or a non-numerical characteristic. In one aspect, a plant has "all but one, two, or three of the physiological and morphological characteristics" of a referred-to-plant, or "all the physiological and morphological characteristics" of Tables 1-2 or "all or all but one, two, or three of the physiological and morphological characteristics" of Tables 1-2.

The physiological and/or morphological characteristics mentioned above are commonly evaluated at significance levels of 1%, 5%, or 10% if they are numerical (quantitative), or for having an identical degree (or type) if not numerical (not quantitative), if measured under the same environmental conditions. For example, a progeny plant or a single locus converted plant or a mutated plant of lettuce variety NUN 09093 LTL may have one or more (or all) of the essential physiological and/or morphological characteristics of said variety listed in Tables 1-2, as determined at the 5% significance level (i.e., p<0.05) for quantitative characteristics and determined by type/degree for non-quantitative characteristics, when grown under the same environmental conditions.

"Distinguishing characteristics" or "distinguishing morphological and/or physiological characteristics" refers herein to the characteristics which distinguish a new variety from other lettuce varieties (i.e., are different), when grown under the same environmental conditions. The distinguishing characteristics between lettuce variety NUN 09093 LTL and the Reference Variety are described Table 3. When comparing lettuce variety NUN 09093 LTL with different varieties, the distinguishing characteristics may be different. In one aspect, the distinguishing characteristics may therefore include at least one, two, three or more (or all) of the characteristics listed in Tables 1-2. All numerical distinguishing characteristics are statistically significantly different at p<0.05 between lettuce variety NUN 09093 LTL and the other variety (e.g., the Reference Variety).

Lettuce Variety NUN 09093 LTL has the following distinguishing characteristics when compared to the Reference Variety as shown in Table 3: 1) white seed color; 2) fewer leaves; 3) smaller plant spread of frame leaves; 4) shorter plant height; 5) lighter plant weight; 6) smaller plant diameter; 7) longer fourth leaf length; 8) smaller fourth leaf width; 9) dentate fourth leaf apical margin; 10) moderate yellow green fourth leaf color; 11) more leaf divisions; 12) concave shape at longitudinal section of mature leaf; 13) greyish green mature leaf color; 14) less undulation of mature leaf margin; 15) deeper incision of mature leaf margin; 16) deeper secondary margin of mature leaf; 17) flabellate mature leaf venation; 18) shorter mature leaf width; 19) smaller mature leaf width; 20) smaller mature leaf size; 21) shorter height from base of head to apex (core length); and 22) thinner diameter at base of head (core width), when grown under the same environmental conditions.

Thus, a lettuce plant "comprising the distinguishing characteristics of lettuce variety NUN 09093 LTL" (such as a progeny plant) refers herein to a plant which does not differ from said variety in the distinguishing characteristics above. Therefore, in one aspect, the disclosure provides a plant that does not differ from lettuce variety NUN 09093 LTL in the distinguishing characteristics above.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties when grown under the same environmental conditions. A numerical characteristic is considered to be "the same" when the value for a numeric characteristic is not significantly different at the 1% (p<0.01) or 5% (p<0.05) significance level, using T-test Paired Two Sample for Means, a standard method known to the skilled person. A non-numerical characteristic is considered to be "the same" when the values have the same "degree" or "type" when scored using USDA and/or UPOV descriptors, for plants are grown under the same environmental conditions.

In one aspect, a statistical analysis of the quantitative characteristics showing the degree of significance may be provided. Statistical significance is the likelihood that a relationship between two or more variables is caused by something other than chance, i.e., that the differences in the means for quantitative characteristics of lettuce variety NUN 09093 LTL and the Reference Variety are significant or due to chance. For the purpose of proving differences or distinction between lettuce variety NUN 09093 LTL and the Reference Variety, a p-value of 5% (or 0.05) or lower is considered statistically significant. This means that there is only a 5% probability that the observed result could have happened just by chance or random variation.

The statistical analysis is drawn from a small sample of at least 20 plants or plants parts of lettuce variety NUN 09093 LTL and the Reference Variety. Statistical points or parameters such as mean, minimum, median, maximum, and standard deviation are collected from the sample data to analyze where the average is, how varied the data set is, and whether the data is skewed. For the purpose of determining whether the result of a data set is statistically significant, a T-test Paired Sample Means is used, a statistical tool for proving significance in the means of the two groups (e.g., lettuce variety NUN 09093 LTL and the Reference Variety) at 5% significance level (p-value of 5% or 0.05).

The term "traditional breeding techniques" encompasses herein crossing, selfing, selection, doubled haploid production, embryo rescue, protoplast fusion, marker assisted selection, mutation breeding etc. as known to the breeder (e.g., methods other than genetic modification/transformation/transgenic methods, e.g., gene editing), by which, for example, a genetically heritable trait can be transferred from one lettuce line or variety to another.

"Variety" or "cultivar" means a plant grouping within a single botanical taxon of the lowest known rank.

"Plant line" is, for example, an inbred variety or a breeding line which can be used to develop one or more varieties. Both are typically highly homozygous. Progeny obtained by selfing such a plant line has the same phenotype as its parents.

"Inbred variety" refers to an inbred (nearly homozygous) line or seeds thereof. For example, the (nearly homozygous) plant is self-pollinated or the (nearly homozygous) female parent is pollinated with pollen of the same plant line to produce inbred seeds on the female parent.

"Progeny" as used herein refers to a plant obtained from a plant designated NUN 09093 LTL. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another lettuce plant of the same or another variety or line, or wild lettuce plants. A progeny may comprise a mutation or a transgene. A "first generation progeny" is the progeny is directly derived from, obtained from, obtainable from or derivable from the parent plant by, e.g., traditional breeding methods (selfing and/or cross-pollinating) or regeneration (optionally combined with transformation or mutation). Thus, a plant of lettuce variety NUN 09093 LTL is the male parent, the female parent, or both of a first generation progeny of lettuce variety NUN 09093 LTL. Progeny may have all of the physiological and morphological characteristics of lettuce variety NUN 09093 LTL when grown under the same environmental conditions. Using methods such as backcrossing, recurrent selection, mutation or transformation, one or more specific characteristics may be introduced into said variety, or to a plant comprising all but one, two, or three of the morphological and physiological characteristics of lettuce variety NUN 09093 LTL.

"Tissue Culture" refers to a composition comprising isolated cells of the same or a different type or a collection of such cells organized into parts of a plant. Tissue culture of various tissues of lettuce and regeneration of plants therefrom is well known and widely published (see, e.g., Teng et al., HortScience. 1992, 27(9): 1030-1032; Teng et al., HortScience. 1993, 28(6): 669-1671; Zhang et al., Journal of Genetics and Breeding. 1992, 46(3): 287-290). Similarly, methods of preparing cell cultures are known in the art.

"Vegetative propagation," "vegetative reproduction," or "clonal propagation" are used interchangeably herein and mean the method of taking part of a plant and allowing that plant part to form at least roots, and also refer to the plant or plantlet obtained by that method. Optionally, the vegetative propagation is grown into a mature plant.

"Regeneration" refers to the development of a plant from cell culture or tissue culture or vegetative propagation.

"Crossing" refers to the mating of two parent plants. The term encompasses "cross-pollination" and "selfing."

"Selfing" refers to self-pollination of a plant, i.e., the transfer of pollen from the anther to the stigma of the same plant.

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant." The technique can also be used on a parental line of a hybrid.

The terms "gene converted," "conversion plant," or "single locus converted plant" in this context refer to lettuce plants which are developed by traditional backcrossing techniques, e.g., backcrossing, or via genetic engineering (e.g., gene editing) or through mutation breeding, wherein essentially all of the desired morphological and physiological characteristics of parent variety or line are recovered, in addition to the one or more characteristics introduced into the parent via e.g., backcrossing technique (optionally including reverse synthesis of breeding line). It is understood that only the addition of a further characteristic (e.g., addition of gene conferring a further characteristic, such as a disease resistance gene), but also the replacement/modification of an existing characteristic by a different characteristic is encompassed herein (e.g., a mutant allele of a gene can modify the phenotype of a characteristic).

Likewise, a "Single Locus Converted (Conversion) Plant" refers to plants developed by plant breeding techniques comprising or consisting of mutation breeding and/or by genetic transformation (e.g., gene editing) and/or by traditional breeding techniques, such as backcrossing, wherein essentially all of the desired morphological and physiological characteristics of a lettuce variety are recovered in addition to the characteristics of the single locus having been transferred into the variety via the above-mentioned techniques, or wherein a morphological and physiological characteristic of the variety has been replaced/modified in the variety. In case of a hybrid, the gene may be introduced, or modified, in the male or female parental line.

"Transgene" refers to a genetic locus comprising a DNA sequence which has been introduced into the genome of a lettuce plant by transformation. A plant comprising a transgene stably integrated into its genome is referred to as "transgenic plant."

"Locus" (plural loci) refers to the specific location of a gene or DNA sequence on a chromosome. A locus may confer a specific trait.

"Genotype" refers to the genetic composition of a cell or organism.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

"Average" refers herein to the arithmetic mean.

The term "mean" refers to the arithmetic mean of several measurements. The mean, if not indicated otherwise within this application, refers to the arithmetic mean of measurements on at least 20 different, randomly selected plants of a variety or line.

DETAILED DESCRIPTION OF VARIOUS ASPECTS OF THE DISCLOSURE

The disclosure relates to the plant of lettuce variety NUN 09093 LTL, wherein a representative sample of seeds of said variety has been deposited under Budapest Treaty, with Accession Number NCIMB 43767. NUN 09093 LTL is a leaf lettuce variety of the Frillice type and is suitable for growing in the open field.

In another aspect, the plant of lettuce variety NUN 09093 LTL, or part thereof, or a progeny thereof comprises resistance to Downy Mildew (*Bremia lactucae*) Isolates Bl:16-33EU, *Nasonovia ribisnigri* Biotype Nr:0, and *Fusarium oxysporum* f. sp. *lactucae* Race 1 IR, measured according to UPOV standards described in TG/13/11.

The disclosure also provides a lettuce plant or part thereof having all of the physiological and morphological characteristics of lettuce variety NUN 09093 LTL, when grown under the same environmental conditions.

The disclosure also provides a plant of lettuce variety NUN 09093 LTL or a progeny plant thereof comprising all of the morphological and/or physiological characteristics (i.e., average values, as indicated on the USDA Objective Description of variety—lettuce (unless indicated otherwise)) as shown in Tables 1-2, when grown under the same environmental conditions. A part of this plant is also provided.

The disclosure further provides a lettuce plant which does not differ from the physiological and morphological characteristics of the plant of lettuce variety NUN 09093 LTL, as determined at the 1%, 2%, 3%, 4%, or 5% significance level for numerical characteristics and determined by degree/type for non-numerical characteristics, when grown under the same environmental conditions. In a particular aspect, the plants are measured in the same trial (e.g., the trial is conducted as recommended by the USDA or UPOV). The disclosure also comprises part of said plant, preferably a leaf or a part thereof.

The morphological and/or physiological differences between two different individual plants described herein (e.g., between lettuce variety NUN 09093 LTL and a progeny of lettuce variety NUN 09093 LTL) or between a plant of lettuce variety NUN 09093 LTL or progeny of said variety, or a plant having all, or all but 1, 2, or 3 of the physiological and morphological characteristics of lettuce variety NUN 09093 LTL (or all, or all but 1, 2, or 3 of the characteristics as listed in Tables 1-2) and another known variety can easily be established by growing said variety next to the each other or next to the other variety (e.g., in the same field, under the same environmental conditions), preferably in several locations which are suitable for said lettuce cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA), whereby various characteristics, for example, plant height, plant head diameter, plant weight, leaf attitude, number of leaf divisions, leaf shape, leaf color, leaf glossiness, leaf thickness, leaf blistering, undulation of margin, leaf venation, head size, head shape, harvest maturity, bolting, disease resistance, insect resistance, and resistance to physiological stress can be measured and directly compared for species of lettuce.

Thus, the disclosure comprises a lettuce plant having one, two, or three of the physiological and/or morphological characteristics which are different from those of the plant of lettuce variety NUN 09093 LTL, and which otherwise has all of the physiological and morphological characteristics of the plant of lettuce variety NUN 09093 LTL (e.g., at 5% significance level for numerical characteristics and identical (same degree or type) for non-numerical characteristics) for plants grown under the same environmental conditions. In one aspect, the different characteristic(s) is/are a result of breeding with lettuce variety NUN 09093 LTL and selection of a progeny plant comprising one, two, or three characteristics which are different than in lettuce variety NUN 09093 LTL. In another aspect, the different characteristic is the result of a mutation (e.g., spontaneous mutation or a human induced mutation through e.g., targeted mutagenesis or traditional mutagenesis such as chemically or radiation induced mutagenesis), or it is the result of transformation.

The disclosure also relates to lettuce variety NUN 09093 LTL, which when compared to the Reference Variety has the following distinguishing characteristics as shown in Table 3: 1) white seed color; 2) fewer leaves; 3) smaller plant spread of frame leaves; 4) shorter plant height; 5) lighter plant weight; 6) smaller plant diameter; 7) longer fourth leaf length; 8) smaller fourth leaf width; 9) dentate fourth leaf apical margin; 10) moderate yellow green fourth leaf color;

11) more leaf divisions; 12) concave shape at longitudinal section of mature leaf; 13) greyish green mature leaf color; 14) less undulation of mature leaf margin; 15) deeper incision of mature leaf margin; 16) deeper secondary margin of mature leaf; 17) flabellate mature leaf venation; 18) shorter mature leaf width; 19) smaller mature leaf width; 20) smaller mature leaf size; 21) shorter height from base of head to apex (core length); and 22) thinner diameter at base of head (core width), when the numerical characteristics are determined at the 5% significance level and determined by type or degree for non-numerical characteristics for plants grown under the same environmental conditions. Also encompassed are parts of that plant.

The disclosure also relates to a seed of lettuce variety NUN 09093 LTL, wherein a representative sample of said seed has been deposited under the Budapest Treaty with Accession Number NCIMB 43767.

In another aspect, a seed of hybrid variety NUN 09093 LTL is obtainable by crossing the male parent of lettuce variety NUN 09093 LTL with the female parent of lettuce variety NUN 09093 LTL and harvesting the seeds produced on the female parent. The resultant seed of said variety can be grown to produce plants of said variety.

In another aspect, the disclosure provides a lettuce plant grown from a seed of lettuce variety NUN 09093 LTL and a plant part thereof.

The disclosure also provides a lettuce head and/or a lettuce leaf produced on a plant grown from a seed of lettuce variety NUN 09093 LTL.

In another aspect, the disclosure provides for a plant part of lettuce variety NUN 09093 LTL, preferably a head or a leaf, a representative sample of seed from said variety has been deposited under Accession Number NCIMB 43767.

Also provided is a plant of lettuce variety NUN 09093 LTL, or a head or a leaf or other plant part thereof, produced from a seed, wherein a representative sample of said seeds has been deposited under the Budapest Treaty, with Accession Number NCIMB 43767.

Also provided is a plant part obtained from variety NUN 09093 LTL, wherein said plant part is a leaf, a part of a leaf, a head, a part of a head, a fruit, a part of a fruit, pollen, an ovule, a cell, a petiole, a shoot or a part thereof, a stem or a part thereof, a root or a part thereof, a root tip, a cutting, a seed, a part of a seed, seed coat, or another maternal tissue which is part of a seed grown on a said variety, a hypocotyl, a cotyledon, a pistil, an anther, or a flower or a part thereof. Such plant parts may be suitable for sexual reproduction (e.g., pollen, a flower, an ovary, an ovule, an embryo, etc.), vegetative reproduction (e.g., a cutting, a root, a stem, a cell, a protoplast, a leaf, a cotyledon, a meristem, etc.), or tissue culture (e.g., a leaf, a pollen, an embryo, a cotyledon, a hypocotyl, a cell, a root, a root tip, an anther, a flower, a seed, a stem, etc.). Heads and leaves are particularly important plant parts.

In a further aspect, the plant part obtained from variety NUN 09093 LTL is a cell, optionally a cell in a cell or tissue culture. The cell may be grown into a plant of lettuce variety NUN 09093 LTL. A part of lettuce variety NUN 09093 LTL (or of a progeny of that variety or of a plant having all of the physiological and morphological characteristics but one, two, or three of lettuce variety NUN 09093 LTL) further encompasses any cells, tissues, organs obtainable from the seedlings or plants in any stage of maturity.

The disclosure also provides a tissue or cell culture comprising regenerable cells of lettuce variety NUN 09093 LTL. Such tissue culture can, for example, be grown on plates or in liquid culture or be frozen for long term storage. The cells of lettuce variety NUN 09093 LTL used to start the culture can be any plant part suitable for vegetative reproduction, or, in a particular aspect, can be one or more of: an embryo, a meristem, a cotyledon, a hypocotyl, a pollen, a leaf, an anther, a root, a root tip, a petiole, a flower, a fruit, a seed, or a stem. In another particular aspect, the tissue culture does not contain somaclonal variation or has reduced somaclonal variation. The skilled person is familiar with methods to reduce or prevent somaclonal variation, including regular reinitiation.

In another aspect, the disclosure provides a lettuce plant regenerated from the tissue or cell culture of lettuce variety NUN 09093 LTL, wherein the regenerated plant is not different from lettuce variety NUN 09093 LTL in all, or all but one, two, or three, of the physiological and morphological characteristics (e.g., determined at the 5% significance level for numerical characteristics and determined by degree/type for non-numerical characteristics) when grown under the same environmental conditions. Optionally, the plant has one, two, or three physiological or morphological characteristic that is different from lettuce variety NUN 09093 LTL, wherein the difference or modification is effected by mutation or transformation with a transgene.

In another aspect, the disclosure provides a lettuce plant regenerated from the tissue or cell culture of variety NUN 09093 LTL, wherein the plant has all or all but one, two, or three of the physiological and morphological characteristics of said variety (e.g., determined at the 5% significance level for numerical characteristics and determined by degree/type for non-numerical characteristics) when grown under the same environmental conditions. Similarity or difference of a characteristic is determined by measuring the characteristics of a representative number of plants grown under the same environmental conditions, determining whether type/degree characteristics are the same and determining whether numerical characteristics are different at the 5% significance level.

Lettuce variety NUN 09093 LTL, or its progeny, or a plant having all physiological and/or morphological characteristics or all but one, two, or three which are different from those of lettuce variety NUN 09093 LTL, can also be reproduced using vegetative reproduction methods. Therefore, the disclosure provides for a method of producing a plant or plant part of lettuce variety NUN 09093 LTL, comprising vegetative reproduction of lettuce variety NUN 09093 LTL. Vegetative propagation comprises regenerating a whole plant from a plant part of lettuce variety NUN 09093 LTL or from a progeny or from a plant having all of the physiological and morphological characteristics of said variety or all but one, two, or three different characteristics, such as a cutting, a cell culture, or a tissue culture.

The disclosure also provides methods of vegetatively propagating a part of the plant of variety NUN 09093 LTL. In certain aspects, the method comprises: (a) cultivating tissue or cells capable of being propagated from lettuce variety NUN 09093 LTL to obtain proliferated shoots; and (b) rooting said proliferated shoots, to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plant. In one aspect, the method further comprises (c) growing plants from said rooted plantlets. Therefore, the method also comprises regenerating a whole plant from a part of lettuce variety NUN 09093 LTL. In a particular aspect, the part to be propagated is a cutting, a cell culture, or a tissue culture.

The disclosure also provides for a vegetatively propagated plant of variety NUN 09093 LTL (or from progeny of lettuce variety NUN 09093 LTL or from a plant having all but one, two, or three of the physiological and/or morphological characteristics of lettuce variety NUN 09093 LTL), wherein the plant has all of the physiological and morphological characteristics of lettuce variety NUN 09093 LTL (e.g., determined at the 5% significance level for numerical characteristics and determined by type/degree for non-numerical characteristics) for plants grown under the same environmental conditions. In another aspect, the propagated plant has all but one, two, or three of the physiological and morphological characteristics of lettuce variety NUN 09093 LTL (e.g., determined at the 5% significance level for numerical characteristics and determined by type/degree for non-numerical characteristics) for plants grown under the same environmental conditions. A part of said propagated plant or said propagated plant with one, two, or three differences is also provided. In another aspect, the propagated plant has all or all but one, two, or three of the physiological and morphological characteristics of lettuce variety NUN 09093 LTL (e.g., as listed in Tables 1-2).

In another aspect, the disclosure provides a method for producing a lettuce plant part, preferably a head or a leaf, comprising growing a plant of lettuce variety NUN 09093 LTL until it develops at least one leaf or develops a head, and optionally collecting the head or leaf Preferably, the head or leaf is collected at harvest maturity. In another aspect, the leaf is collected at baby leaf stage.

In another aspect, a plant of lettuce variety NUN 09093 LTL can be produced by seeding directly in the soil (e.g., field) or by germinating the seeds in controlled environment conditions (e.g., greenhouses, hydroponic cultures, etc.) and optionally transplanting the seedlings into the field (see, e.g., Gonai et al., J. of Exp. Bot., 55(394): 111, 2004; Turini, et. al., University of California Agricultural and Natural Resources, 2011, Publication 7215, 1-6; Smith, et. al., University of California Agricultural and Natural Resources, 2011, Publication 7216, 1-6). Lettuce may also be grown in tunnels. Moreover, said variety can be grown in hydroponic cultures as described in, e.g., US 2008/0222949, which is herein incorporated by reference in its entirety, and the skilled person is familiar with various types of hydroponic cultures. Alternatively, seed of lettuce variety NUN 09093 LTL may be grown on peat block for use as root ball lettuce. Furthermore, said variety may be combined with 1, 2 or 3 different lettuce varieties to be grown as "composite lettuce" (see, e.g., EP 1197137, which is herein incorporated by reference in its entirety).

In still another aspect, the disclosure provides a method of producing a lettuce plant, comprising crossing a plant of lettuce variety NUN 09093 LTL with a second lettuce plant at least once, allowing the seed to develop and optionally harvesting said progeny seed. The skilled person can select a progeny lettuce plant from said crossing. Optionally, the progeny (grown from the progeny seed) is crossed twice, thrice, or four, six, or seven times, and allowed to set seed. In one aspect, the first "crossing" further comprises planting seeds of a first and a second parent lettuce plant, often in proximity so that pollination will occur, for example, mediated by insect vectors. Alternatively, pollen can be transferred manually. Where the plant is self-pollinated, pollination may occur without the need for direct human intervention other than plant cultivation. After pollination, the plant can produce seed.

The disclosure also provides a method for collecting pollen of lettuce variety NUN 09093 LTL, comprising collecting pollen from a plant of variety NUN 09093 LTL. Alternatively, the method comprises growing a plant of lettuce variety NUN 09093 LTL until at least one flower contains pollen and collecting the pollen. In a particular aspect, the pollen is collected when it is mature or ripe. A suitable method for collecting pollen comprises collecting anthers or the part of the anther that contains pollen, for example, by cutting the anther or the part of the anther off. Pollen can be collected in a container. Optionally, collected pollen can be used to pollinate a lettuce flower.

In yet another aspect, the disclosure provides a method of producing a lettuce plant, comprising selfing a plant of variety NUN 09093 LTL one or more times, and selecting a progeny plant from said selfing. In one aspect, the progeny plant retains all or all but one, two, or three of the physiological and morphological characteristics of lettuce variety NUN 09093 LTL when grown under the same environmental conditions. In a different aspect, the progeny plant comprises all (or all but one, two or three) of the physiological and morphological characteristic of lettuce variety NUN 09093 LTL of Tables 1-2.

The disclosure also provides a method for developing a lettuce plant in a lettuce breeding program, using lettuce variety NUN 09093 LTL, or its parts as a source of plant breeding material. Suitable plant breeding techniques are recurrent selection, backcrossing, pedigree breeding, mass selection, mutation breeding, genetic marker enhanced selection, and/or genetic transformation. In one aspect, the method comprises crossing lettuce variety NUN 09093 LTL or progeny of said variety, or a plant comprising all but 1, 2, or 3 or more of the morphological and physiological characteristics of lettuce variety NUN 09093 LTL (e.g., as listed in Tables 1-2) with a different lettuce plant, and wherein one or more offspring of the crossing are subject to one or more plant breeding techniques: recurrent selection, backcrossing, pedigree breeding, mass selection, mutation breeding, genetic marker enhanced selection, genetic transformation (see, e.g., Brotman et al., Theor Appl Genet (2002) 104: 1055-1063). For breeding methods in general, see, e.g., Acquaah, Principles of Plant Genetics and Breeding, 2007, Blackwell Publishing, ISBN-13: 978-1-4051-2646-4.

In other aspects, the disclosure provides for a progeny plant of variety NUN 09093 LTL such as a progeny plant obtained by further breeding of lettuce variety NUN 09093 LTL. Further breeding with said variety includes selfing and/or cross-pollinating lettuce variety NUN 09093 LTL with another lettuce plant or variety one or more times. In a particular aspect, the disclosure provides for a progeny plant that retains all of the morphological and physiological characteristics of lettuce variety NUN 09093 LTL, optionally all or all but one, two, or three characteristics as listed in Tables 1-2, determined at the 5% significance level for numerical characteristics and determined by type/degree for non-numerical characteristics, when grown under the same environmental conditions. In another aspect, the progeny is a first generation progeny, i.e., the ovule or the pollen (or both) used in the crossing is an ovule or pollen of lettuce variety NUN 09093 LTL, where the pollen comes from an anther of lettuce variety NUN 09093 LTL and the ovule comes from an ovary of lettuce variety NUN 09093 LTL.

In another aspect, the plant and plant parts of lettuce variety NUN 09093 LTL and progeny of said variety are provided, e.g., grown from seeds, produced by sexual or vegetative reproduction, regenerated from the above-described plant parts, or regenerated from a cell or tissue culture of lettuce variety NUN 09093 LTL, in which the reproduced (seed propagated or vegetatively propagated)

plant has all of the physiological and morphological characteristics of lettuce variety NUN 09093 LTL, e.g., as listed in Tables 1-2. In one aspect, said progeny of lettuce variety NUN 09093 LTL can be modified in one, two, or three characteristics, in which the modification is a result of mutagenesis or transformation with a transgene.

In one aspect, pedigree selection is used as a breeding method for developing a lettuce variety. Pedigree selection is also known as the "Vilmorin System of Selection," see, e.g., Allard, John Wiley & Sons, Inc., 1999, 64-67. In general, selection is first practiced among F2 plants. In the next season, the most desirable F3 lines are first identified, then desirable F3 plants within each line are selected. The following season and in all subsequent generations of inbreeding, the most desirable families are identified first, then desirable lines within the selected families are chosen. A family refers to lines that were derived from plants selected from the same progeny from the preceding generation.

Using pedigree method, two parents may be crossed using an emasculated female and a pollen donor (male) to produce F1 offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization. The F1 may be self-pollinated to produce segregating F2 generation. Individual plants may then be selected which represent the desired phenotype in each generation (F3, F4, F5, etc.) until the traits are homozygous or fixed within a breeding population.

Thus, progeny in connection with pedigree selection are either the generation (seeds) produced from the first cross (F1) or selfing (S1), or any further generation produced by crossing and/or selfing (F2, F3, F4, F5, F6, F7, etc.) and/or backcrossing (BC1, BC2, BC3, BC4, BC5, BC6, BC7, etc.) one or more selected plants of the F1 and/or S1 and/or BC1 generation (or plants of any further generation, e.g., the F2) with another lettuce plant (an/or with wild relative of lettuce).

In yet another aspect, the disclosure provides for a method of producing a new lettuce plant. The method comprises crossing lettuce variety NUN 09093 LTL, or a plant of comprising all but 1, 2, or 3 of the morphological and physiological characteristics of said lettuce variety (as listed in Tables 1-2), or a progeny plant thereof, either as male or as female parent, with a second lettuce plant (or a wild relative of lettuce) one or more times, and/or selfing a lettuce plant of variety NUN 09093 LTL, or a progeny plant thereof, one or more times, and selecting progeny from said crossing and/or selfing. The second lettuce plant may, for example, be a line or variety of the species *Lactuca sativa*, or other *Lactuca* species.

In a further aspect, lettuce variety NUN 09093 LTL is used in crosses with other, different, lettuce varieties to produce first generation (F1) lettuce hybrid seeds and plants with superior characteristics. In a particular aspect, the disclosure provides a method a producing a hybrid lettuce seed comprising crossing a first parent lettuce plant with a second parent lettuce plant and harvesting the resultant seed, in which the first parent lettuce plant or second parent lettuce plant is lettuce variety NUN 09093 LTL. Also provided is a hybrid lettuce seed produced from crossing a first parent lettuce plant with a second parent lettuce plant and harvesting the resultant hybrid lettuce seed, wherein said first parent lettuce plant or second parent lettuce plant is lettuce variety NUN 09093 LTL. In a further aspect, the hybrid lettuce plant produce from the hybrid lettuce seed is provided.

The morphological and physiological characteristics (and the distinguishing characteristics) of lettuce variety NUN 09093 LTL are provided, for example, in Tables 1-2. Encompassed herein is also a plant obtainable from lettuce variety NUN 09093 LTL (e.g., by selfing and/or crossing and/or backcrossing with said variety and/or progeny of said variety) comprising all or all but one, two or three of the physiological and morphological characteristics of lettuce variety NUN 09093 LTL listed in Tables 1-2 (e.g., determined at the 5% significance level for numerical characteristics and determined by type/degree for non-numerical characteristics) when grown under the same environmental conditions and/or comprising one or more (or all; or all except one, two or three) when grown under the same environmental conditions. The morphological and/or physiological characteristics may vary somewhat with variation in the environment (e.g., temperature, light intensity, day length, humidity, soil, fertilizer use), which is why a comparison under the same environmental conditions is preferred. Colors can best be measured against the Royal Horticultural Society (RHS) Chart.

In another aspect, a seed of inbred variety NUN 09093 LTL is obtainable by selfing the variety and harvesting the seeds produced. The resultant seeds can be grown to produce plants of said variety.

In still another aspect, the disclosure provides a method of producing a plant derived from lettuce variety NUN 09093 LTL, the method comprising: (a) preparing a progeny plant derived from lettuce variety NUN 09093 LTL by crossing a plant of variety NUN 09093 LTL either as a male or female parent with a second plant or selfing lettuce variety NUN 09093 LTL or vegetative reproduction of lettuce variety NUN 09093 LTL, and (b) collecting seeds from said crossing or selfing or regenerating a whole plant from the vegetative cell-or tissue culture. Also provided are seeds and/or plants obtained by this method. All plants produced using lettuce variety NUN 09093 LTL as a parent are within the scope of the disclosure, including plant parts derived from lettuce variety NUN 09093 LTL.

In further aspects, the method comprises growing a progeny plant of a subsequent generation from said seed of a progeny plant of a subsequent generation and crossing the progeny plant of a subsequent generation with itself or a second plant and repeating the steps for an additional 3-10 generations to produce a plant derived from lettuce variety NUN 09093 LTL. The plant derived from lettuce variety NUN 09093 LTL may be an inbred line and the aforementioned repeating crossing steps may be defined as comprising sufficient inbreeding to produce the inbred line. By selecting plants having one or more desirable traits, a plant derived from lettuce variety NUN 09093 LTL is obtained which has some of the desirable traits of the line as well as potentially other selected traits.

The disclosure provides for methods of producing plants which retain all the morphological and physiological characteristics of a plant described herein. The disclosure also provides for methods of producing a plant comprising all but 1, 2, or 3 or more of the morphological and physiological characteristics of lettuce variety NUN 09093 LTL (e.g., as listed in Tables 1-2), but which are still genetically closely related to said variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to lettuce variety NUN 09093 LTL if its DNA fingerprint is at least 80%, 90%, 95% or 98% identical to the fingerprint of lettuce variety NUN 09093 LTL. In a particular aspect, AFLP markers are used for DNA fingerprinting (see, e.g., Vos et al. 1995, Nucleic Acid Research 23: 4407-4414). A closely related plant may have a Jaccard's Similarity index of at least about 0.95 or 0.96 or more (see, e.g., "Guidelines for the Handling of a Dispute on Essential Derivation in Lettuce" at worldseed.org/wp-content/uploads/2015/10/Guidelines EDV_Lettuce_2004.pdf). the disclosure also provides a plant and a variety obtained or selected by applying these methods on lettuce variety NUN 09093 LTL. Such a plant may be produced by crossing and/or selfing, or alternatively, a plant may simply be identified and selected amongst plants of said variety, or progeny of said variety, e.g., by identifying a variant within lettuce variety NUN 09093 LTL or progeny of said variety (e.g., produced by selfing) which variant differs from lettuce variety NUN 09093 LTL in one, two or three of the morphological and/or physiological characteristics (e.g., characteristics listed in Tables 1-2). In one aspect, the disclosure provides a plant of lettuce variety NUN 09093 LTL having a Jaccard's Similarity index with said variety of at least 0.95, 0.96, 0.97, 0.98 or even at least 0.99.

In another aspect, the disclosure provides a lettuce plant comprising genomic DNA having at least 95%, 96%, 97%, 98%, or 99% sequence identity compared to the genomic DNA sequence of a plant of lettuce variety NUN 09093 LTL as deposited under Accession Number NCIMB 43767. In another aspect, the lettuce plant further comprises all or all but one, two, or three of the physiological and morphological characteristics of lettuce variety NUN 09093 LTL (e.g., as listed in Tables 1-2). In other aspects, the lettuce plant comprises the distinguishing characteristics of lettuce variety NUN 09093 LTL.

For the purpose of this disclosure, the "sequence identity" or nucleotide sequences, expressed as a percentage, refers to the number of positions in the two optimally aligned sequences which have identical residues (×100) divided by the number of positions compared. A gap, i.e., a position in the pairwise length where a residue is present in one sequence but not in the other, is regarded as a position with non-identical residues. A pairwise global sequence alignment of two nucleotide sequences is found by aligning the two consequences over the entire length according to the Needleman and Wunsch global alignment algorithm described in Needleman and Wunsch, 1970, J. Mol. Bio. 48(3):443-53. A full implementation of the Needleman-Wunsch global alignment algorithm is found in the needle program in The European Molecular Biology Open Software (see, EMBOSS, Rice, et. al., Trends in Genetics, June 2000, 16(6):276-77).

In another aspect, the plant of lettuce variety NUN 09093 LTL may also be mutated (by e.g., irradiation, chemical mutagenesis, heat treatment, etc.) and mutated seeds or plants may be selected in order to change one or more characteristics of said variety. Methods such as TILLING (Targeting Induced Local Lesions in Genomes) may be applied to lettuce populations in order to identify mutants.

Similarly, lettuce variety NUN 09093 LTL may be transformed and regenerated, whereby one or more chimeric genes are introduced into the variety or into a plant comprising all but one, two, or three of the physiological and morphological characteristics (e.g., as listed in Tables 1-2). Many useful traits can be introduced into lettuce variety NUN 09093 LTL by e.g., crossing lettuce variety NUN 09093 LTL with a transgenic lettuce plant comprising a desired transgene, as well as by directly introducing a transgene into lettuce variety NUN 09093 LTL by genetic transformation techniques.

Any pest or disease resistance genes may be introduced into lettuce variety NUN 09093 LTL, progeny of said variety, or into a plant comprising all but 1, 2, or 3 or more of the morphological and physiological characteristics of lettuce variety NUN 09093 LTL (e.g., as listed in Tables 1-2). Resistance to one or more of the following diseases or pests may be introduced into the plant described herein: *Rhizomonas suberifaciens* (Corky root rot), *Bremia lactucae* (Downy mildew), *Erysiphe cichoracearum* f. sp. *lactucae* (Powdery mildew), *Sclerotinia minor* and *Sclerotinia sclerotiorum* (Lettuce Drop), *Pseudomonas* spp. (Bacterial Soft Rot), *Botrytis cinerea* (Grey Mold), *Verticillium dahlia* (*Verticillium* Wilt), *Xanthomonas* spp. (Bacterial Leaf Spot), *Microdochium panattonianum* (Anthracnose), *Fusarium oxysporum* f. sp. *lactucae, Rhizoctonia solani* (Bottom Rot), Cabbage Loopers, Lettuce Root Aphid, *Myzus persicae* (Green Peach Aphid), *Liriomyza langei* (Pea Leafminer), *Liriomyza trifolii* (Serpentine Leafminer), *Liriomyza sativae* (Vegetable Leafminer), Foxglove Aphid, Potato Aphid, Beet Armyworm, *Bemisia argentifolii* (Silver Whitefly), and/or Aster Yellows. Other resistance genes, against pathogenic viruses (e.g., Mirafiori Lettuce Big Vein Virus (LMBVV), Lettuce Infectious Yellows Virus (LIYV), Lettuce Mosaic Virus (LMV), Lettuce Necrotic Stunt Virus (LNSV), Cucumber Mosaic Virus (CMV), Tomato Bushy Stunt Virus (Dieback), Tomato Spotted Wilt Virus (TSWV), Turnip Mosaic Virus, Beet Western Yellows Virus (BWYV), Alfalfa mosaic virus (AMV)), fungi, bacteria, nematodes, insects or other pests may also be introduced. In one aspect, resistance against *Nasonovia ribisnigri* biotype Nr:0 and/or Nr:1 maybe introduced into the plant disclosed herein. Also, any resistances to physiological stresses may be introduced into the plant described herein, or progeny thereof or into a plant comprising all but 1, 2, or 3 or more of the morphological and physiological characteristics of said plant (e.g., as listed in Tables 1-2). Resistance against one or more of the following may be introduced into the plant described herein: Tip burn, Heat, Drought, Cold, Salt and/or Brown rob (Rib Discoloration/Rib Blight).

Genetic transformation may, therefore, be used to insert a selected transgene into the lettuce plants of the disclosure described herein or may, alternatively, be used for the preparation of transgenic lettuce plants which can be used as a source of the transgene(s), which can be introduced into lettuce variety NUN 09093 LTL by e.g., backcrossing. A genetic trait which has been engineered into the genome of a particular lettuce plant may then be moved into the genome of another lettuce plant (e.g., another variety) using traditional breeding techniques which are well known in the art. For example, backcrossing is commonly used to move a transgene from a transformed lettuce variety into an already developed lettuce variety and the resulting backcross conversion plant will then comprise the transgene(s).

Any DNA sequences, whether from a different species or from the same species, which are inserted into the genome using transformation, are referred to herein collectively as "transgenes." A "transgene" also encompasses antisense, or sense and antisense sequences capable of gene silencing. Thus, the disclosure also relates to transgenic plants of lettuce variety NUN 09093 LTL. In another aspect, a transgenic plant of lettuce variety NUN 09093 LTL may contain at least one transgene but could also contain at least 1, 2, 3, 4, or more transgenes.

Plant transformation involves the construction of an expression vector which will function in plant cells. Such a vector comprises DNA comprising a gene under control of, or operatively linked to a regulatory element active in plant cells (e.g., promoter). The expression vector may contain one or more such operably linked gene/regulatory element combinations. The vector may be in the form of a plasmid and can be used alone or in combination with other plasmids to provide transformed lettuce plants using transformation methods to incorporate transgenes into the genetic material of the lettuce plant(s). Transformation can be carried out using standard methods, such as *Agrobacterium tumefaciens* mediated transformation or biolistic, followed by selection of the transformed cells and regeneration into plants.

Plants can also be genetically engineered, modified, or manipulated to express various phenotypes of horticultural interest. Through the transformation of lettuce, the expression of genes can be altered to enhance disease resistance, insect resistance, herbicide resistance, stress tolerance, horticultural quality, and other traits. Transformation can also be used to insert DNA sequences which control or help control male sterility or fertility restoration. DNA sequences native to lettuce as well as non-native DNA sequences can be transformed into lettuce and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing or gene suppression) is desirable for several aspects of genetic engineering in plants.

Genome editing is another method recently developed to genetically engineer plants. Specific modification of chromosomal loci or targeted mutation can be done through sequence-specific nucleases (SSNs) by introducing a targeted DNA double strand break in the locus to be altered. Examples of SSNs that have been applied to plants are: finger nucleases (ZFNs), transcription activator-like effector nucleases (TALENs), engineered homing endonucleases or meganucleases, and clustered regularly interspaced short palindromic repeats (CRISPR)/CRISPR-associated protein 9 (Cas9), see, e.g., Songstad, et. al., Critical Reviews in Plant Sciences, 2017, 36:1, 1-23.

Thus, the disclosure provides a method of producing a lettuce plant having a desired trait, comprising mutating a plant or plant part of variety NUN 09093 LTL, optionally with a target gene, and selecting a plant the desired trait, wherein the mutated plant retains all or all but one, two, or three of the physiological and morphological characteristics of said variety, optionally as described Tables 1-2, and contains the desired trait, and wherein a representative sample of seed of variety NUN 09093 LTL has been deposited under Accession Number NCIMB 43767. In one aspect, the target genes of interest for lettuce are genes affecting tissue discoloration or wound-induced surface discoloration (see, e.g., WO/2017/144669), plant susceptibility genes (see, e.g., WO/2008/092505, U.S. Pat. No. 8,237, 019), seed germination, male sterility, among others. In a further aspect, the desired trait is yield, nutritional value, taste, color, crunchiness, male sterility, herbicide tolerance, insect resistance, pest resistance, disease resistance, environmental stress tolerance, modified carbohydrate metabolism, or modified protein metabolism, or the mutation occurs in any of the following genes: Ferulate-5-hydroxylase, dmr1, dmr6, NCED4, PAL, PPO.

The disclosure also provides a method for inducing a mutation in lettuce variety NUN 09093 LTL comprising:
a. exposing the seed, plant, plant part, or cell of lettuce variety NUN 09093 LTL to a mutagenic compound or to radiation, wherein a representative sample of seed of said variety has been deposited under Accession Number NCIMB 43767;
b. selecting the seed, plant, or plant part or cell of lettuce variety NUN 09093 LTL having a mutation; and
c. optionally growing and/or multiplying the seed, plant, plant part, or cell of lettuce variety NUN 09093 LTL having the mutation.

The disclosure also provides a method of producing a lettuce plant having a desired trait, wherein the method comprises transforming the lettuce plant with a transgene that confers the desired trait, wherein the transformed plant otherwise retains all of the physiological and morphological characteristics of the plant of variety NUN 09093 LTL and contains the desired trait. Thus, a transgenic lettuce plant is provided which is produced by the method described above, wherein the plant comprises the desired trait and has all of the physiological and morphological characteristics of the plant of variety NUN 09093 LTL.

In another aspect, the disclosure provides a method of producing a progeny of plant of variety NUN 09093 LTL further comprising a desired trait, said method comprising transforming the plant of lettuce variety NUN 09093 LTL with at least one transgene that confers the desired trait and/or crossing the plant of lettuce variety NUN 09093 LTL with a transgenic lettuce plant comprising a desired transgene so that the genetic material of the progeny that resulted from the cross contains the desired transgene(s). Also encompassed is the progeny produced by this method.

A desired trait (e.g., gene(s) conferring pest or disease resistance, herbicide, fungicide or insecticide tolerance, etc.) can be introduced into lettuce variety NUN 09093 LTL, or progeny of said variety, by transforming said variety or progeny of said variety with a transgene that confers the desired trait, wherein the transformed plant retains all or all but one, two or three of the phenotypic and/or morphological and/or physiological characteristics of lettuce variety NUN 09093 LTL or the progeny of said variety and contains the desired trait, wherein the desired trait is yield, nutritional value, taste, color, crunchiness, male sterility, herbicide tolerance, insect resistance, pest resistance, disease resistance, environmental stress tolerance, modified carbohydrate metabolism, or modified protein metabolism or the mutation occurs in any of the following genes: Ferulate-5-hydroxylase, dmr1, dmr6, NCED4, PAL, PPO. In a particular aspect, the specific transgene may be any known in the art or listed herein, including, a polynucleotide sequence conferring resistance to imidazolinone, sulfonylurea, glyphosate, glufosinate, triazine, benzonitrile, cyclohexanedione, phenoxy proprionic acid and L-phosphinothricin or a polynucleotide conferring resistance to *Rhizomonas suberifaciens* (Corky root rot), *Bremia lactucae* (Downy mildew), *Erysiphe cichoracearum* f sp. *lactucae* (Powdery mildew), *Sclerotinia minor* and *Sclerotinia sclerotiorum* (Lettuce Drop), *Pseudomonas* spp. (Bacterial Soft Rot), *Botrytis cinerea* (Grey Mold), *Verticillium* dahlia (*Verticillium* Wilt), *Xanthomonas* spp. (Bacterial Leaf Spot), *Microdochium panattonianum* (Anthracnose), *Fusarium oxysporum* f. sp. *lactucae*, *Rhizoctonia solani* (Bottom Rot), Cabbage Loopers, Lettuce Root Aphid, *Myzus persicae* (Green Peach Aphid), *Liriomyza langei* (Pea Leafminer), *Liriomyza trifolii*

(Serpentine Leafminer), *Liriomyza sativae* (Vegetable Leafminer), Foxglove Aphid, Potato Aphid, Beet Armyworm, *Bemisia argentifolii* (Silver Whitefly), and/or Aster Yellows. Other resistance genes, against pathogenic viruses (e.g., Mirafiori Lettuce Big Vein Virus (LMBVV), Lettuce Infectious Yellows Virus (LIYV), Lettuce Mosaic Virus (LMV), Lettuce Necrotic Stunt Virus (LNSV), Cucumber Mosaic Virus (CMV), Tomato Bushy Stunt Virus (Dieback), Tomato Spotted Wilt Virus (TSWV), Turnip Mosaic Virus, Beet Western Yellows Virus (BWYV), Alfalfa mosaic virus (AMV)), fungi, bacteria, nematodes, insects or other pests may also be introduced.

By crossing and/or selfing, (one or more) single traits may be introduced into, or modified in, lettuce variety NUN 09093 LTL (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into lettuce variety NUN 09093 LTL by breeding with said variety.

In another aspect, the disclosure provides a method of introducing a single locus conversion, a single trait conversion, or a desired trait into lettuce variety NUN 09093 LTL, comprising introducing a single locus conversion, a single trait conversion, or a desired trait in at least one of the parents of lettuce variety NUN 09093 LTL, and crossing the converted parent with the other parent of lettuce variety NUN 09093 LTL, to obtain seed of said variety.

In another aspect, the step of introducing a single locus conversion, a single trait conversion, or a desired trait in at least one of the parent plants comprises:
   a. crossing the parental line of lettuce variety NUN 09093 LTL, with a second lettuce plant comprising the single locus conversion, the single trait conversion, or the desired trait;
   b. selecting F1 progeny plants that contain the single locus conversion, the single trait conversion, or the desired trait.
   c. crossing said selected progeny plants of step b) with the parental line of step a) to produce a backcross progeny plant;
   d. selecting backcross progeny plants comprising the single locus conversion, the single trait conversion or the desired trait and otherwise all or all but one, two, or three of the physiological and morphological characteristics of the parental line of step a) to produce selected backcross progeny plants; and
   e. optionally repeating steps c) and d) one or more times in succession to produce selected second, third, or fourth, or higher backcross progeny plants comprising the single locus conversion, the single trait conversion, or the desired trait and otherwise all or all but one, two, or three of the physiological and morphological characteristics of the parental line of step a) to produce selected backcross progeny plants, when grown in the same environmental conditions.

The disclosure further relates to plants obtained by this method.

In another aspect, introducing a single locus conversion, a single trait conversion, or a desired trait in at least one of the parents comprise:
   a. obtaining a cell or tissue culture of cells of the parental line of lettuce variety NUN 09093 LTL;
   b. genetically transforming or mutating said cells;
   c. growing the cells into a plant; and
   d. optionally selecting a plant that contains the desired single locus conversion, single trait conversion, or the desired trait.

In another aspect, the disclosure provides a method of introducing a single locus conversion, a single trait conversion, or a desired trait into lettuce variety NUN 09093 LTL, comprising:
   a. obtaining a combination of parental lines of lettuce variety NUN 09093 LTL, optionally through reverse synthesis of breeding lines;
   b. introducing a single locus conversion, a single trait conversion, or a desired trait in at least one of the parents of step a); and
   c. crossing the converted parent with the other parent of step a) to obtain seed of lettuce variety NUN 09093 LTL.

In any of the above methods, wherein the single locus conversion concerns a trait, the trait may be yield or pest resistance, or disease resistance. In one aspect, the trait is disease resistance and the resistance is conferred to *Rhizomonas suberifaciens* (Corky root rot), *Bremia lactucae* (Downy mildew), *Erysiphe cichoracearum* f. sp. *lactucae* (Powdery mildew), *Sclerotinia minor* and *Sclerotinia sclerotiorum* (Lettuce Drop), *Pseudomonas* spp. (Bacterial Soft Rot), *Botrytis cinerea* (Grey Mold), *Verticillium* dahlia (*Verticillium* Wilt), *Xanthomonas* spp. (Bacterial Leaf Spot), *Microdochium panattonianum* (Anthracnose), *Fusarium oxysporum* f. sp. *lactucae, Rhizoctonia solani* (Bottom Rot), Cabbage Loopers, Lettuce Root Aphid, *Myzus* persicae (Green Peach Aphid), *Liriomyza langei* (Pea Leafminer), *Liriomyza trifolii* (Serpentine Leafminer), *Liriomyza sativae* (Vegetable Leafminer), Foxglove Aphid, Potato Aphid, Beet Armyworm, *Bemisia argentifolii* (Silver Whitefly), and/or Aster Yellows. Other resistance genes, against pathogenic viruses (e.g., Mirafiori Lettuce Big Vein Virus (LMBVV), Lettuce Infectious Yellows Virus (LIYV), Lettuce Mosaic Virus (LMV), Lettuce Necrotic Stunt Virus (LNSV), Cucumber Mosaic Virus (CMV), Tomato Bushy Stunt Virus (Dieback), Tomato Spotted Wilt Virus (TSWV), Turnip Mosaic Virus, Beet Western Yellows Virus (BWYV), Alfalfa mosaic virus (AMV)), fungi, bacteria, nematodes, insects or other pests may also be introduced. In one aspect, resistance against *Nasonovia ribisnigri* biotype Nr:0 and/or Nr:1 maybe introduced into the plant disclosed herein. Also, any resistances to physiological stresses may be introduced into the plant described herein, or progeny thereof or into a plant comprising all but 1, 2, or 3 or more of the morphological and physiological characteristics of said plant (e.g., as listed in Tables 1-2). Resistance against one or more of the following may be introduced into the plant described herein: Tip burn, Heat, Drought, Cold, Salt and/or Brown rob (Rib Discoloration/Rib Blight).

The disclosure also provides a plant having one, two, or three physiological and/or morphological characteristics which are different from those of lettuce variety NUN 09093 LTL, and which otherwise has all of the physiological and morphological characteristics of said variety, wherein a representative sample of seed of said variety has been deposited under Accession Number NCIMB 43767. In particular, variants which differ from lettuce variety NUN 09093 LTL in none, one, two, or three of the characteristics mentioned in Tables 1-2 are encompassed.

The disclosure also provides a lettuce plant comprising at least a set of first set of the chromosomes of lettuce variety NUN 09093 LTL, a sample of seed of said variety has been deposited under Accession Number NCIMB 43767; optionally further comprising a single locus conversion or mutation, wherein said plant has essentially all of the morphological and physiological characteristics of the plant comprising at least a first set of the chromosomes of said variety. In another aspect, the single locus conversion or mutation confers a trait, wherein the trait is yield, color, size, taste, crunchiness, enhance nutritional quality, post-harvest quality, male sterility, herbicide tolerance, insect resistance, pest resistance, disease resistance, environmental stress tolerance, modified carbohydrate metabolism, or modified protein metabolism.

In one aspect, the disclosure provides for a haploid plant and/or a doubled haploid plant of variety NUN 09093 LTL, or a plant having all but one, two or three physiological and/or morphological characteristics of lettuce variety NUN 09093 LTL, or progeny of said variety. Haploid and doubled haploid (DH) plants can, for example, be produced by cell or tissue culture and chromosome doubling agents and regeneration into a whole plant. DH production chromosome doubling may be induced using known methods, such as colchicine treatment or the like. In one aspect, the method comprises inducing a cell or tissue culture with a chromosome doubling agent and regenerating the cells or tissues into a whole plant.

In another aspect, the disclosure comprises a method for producing doubled haploid cells of lettuce variety NUN 09093 LTL, comprising making doubled haploid cells from haploids cells from the plant or plant part of lettuce variety NUN 09093 LTL with a chromosome doubling agent, such as colchicine treatment (see, e.g., Nikolova and Niemirowicz-Szczytt (1996) Acta Soc Bot Pol 65:311-217).

In another aspect, the disclosure provides for haploid plants and/or doubled haploid plants derived from lettuce variety NUN 09093 LTL that, when combined, make a set of parents of lettuce variety NUN 09093 LTL. The haploid plant and/or the doubled haploid plant of variety NUN 09093 LTL can be used in a method for generating parental lines of lettuce variety NUN 09093 LTL.

In one aspect, the disclosure relates to a method of producing a combination of parental lines of a plant of variety NUN 09093 LTL, comprising making double haploid cells from haploid cells form said plant or a seed of that plant; and optionally crossing these parental lines to produce and collect seeds. In another aspect, the disclosure relates to a combination of parental lines produced by this method. In still another aspect, the combination of parental lines can be used to produce a seed or plant of variety NUN 09093 LTL, when these parental lines are crossed. In still another aspect, the disclosure relates to a combination of a parental lines from which a seed or plant having all physiological and/or morphological characteristics of lettuce variety NUN 09093 LTL (e.g., determined at the 5% significance level for numerical characteristics and determined by type/degree for non-numerical characteristics) when grown under the same environmental conditions/

In another aspect, a combination of a male and a female parental line of lettuce variety NUN 09093 LTL can be generated, for example, through reverse synthesis of breeding lines.

Using methods known in the art such as "reverse synthesis of breeding lines" or "reverse breeding", it is possible to produce parental lines for a hybrid plant such as lettuce variety NUN 09093 LTL. A skilled person can take any individual heterozygous plant (called a "phenotypically superior plant" in Example 2 of US 2015/0245570 hereby incorporated by reference in its entirety; lettuce variety NUN 09093 LTL is such plant) and generate a combination of parental lines (reverse breeding parental lines) that, when crossed, produce the variety NUN 09093 LTL. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from US 2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., lettuce variety NUN 09093 LTL), comprising in one aspect: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

In another aspect, the method for producing parental lines for hybrid organisms, e.g., of lettuce variety NUN 09093 LTL, which when crossed reconstitute the genome of lettuce variety NUN 09093 LTL, comprising:
  a. defining a set genetic a) markers that are present a heterozygous form (H) in a partially heterozygous starting organism;
  b. producing at least one further generation from the starting organism by self-pollination (e.g., F2 or F3 generation);
  c. selecting at least one pair of progeny organisms in which at least one genetic marker from the set is present in a complementary homozygous forms (B vs. A, or A vs. B); and optionally repeating steps b) and c) until at least one pair of progeny organisms that have complementary alleles for at least a subset of the genetic markers has been selected as parental lines for a hybrid.

The disclosure also provides methods for determining the identity of parental lines of the plant described herein, in particular the identity of the female line. US 2015/0126380, which is hereby incorporated by reference, relates to a non-destructive method for analyzing maternal DNA of a seed. In this method, the DNA is dislodged from the seed coat surface and can be used to collect information on the genome of the maternal parent of the seed. This method for analyzing maternal DNA of a seed, comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant of lettuce variety NUN 09093 LTL is a progeny of said variety, because the seed coat of the seed is a maternal tissue genetically identical to lettuce variety NUN 09093 LTL. Since lettuce variety NUN 09093 LTL is an inbred variety, with a very high degree of homozygosity, any F1 progeny will inherit the same, predictable, set of chromosomes from its parent. Thus, the skilled person will also be able to identify maternal tissues of a seed grown on an F1 progeny of lettuce variety NUN 09093 LTL, using the methods described in US 2015/0126380. In another particular aspect, the skilled person can determine the identity of the female parental line of lettuce variety NUN 09093 LTL by analyzing the seed coat of a seed of that variety. In another aspect, the skilled person can determine whether a seed is grown on lettuce variety NUN 09093 LTL.

In another aspect, the disclosure provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including SNP (Single Nucleotide Polymorphism) genotyping, restriction fragment length polymorphism identification (RFLP) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads. Alternatively, the entire genome could be sequenced. The method may, in certain aspects, comprise detecting a plurality of polymorphisms in the genome of the plant, for example, by obtaining a sample of nucleic acid from a plant and detecting in said nucleic acids a plurality of polymorphisms. The method may further comprise storing the results of the step of detecting the plurality of polymorphisms on a computer readable medium.

Also provided is a plant part obtainable from variety NUN 09093 LTL (or from progeny of said variety or from a plant having all or all but one, two, or three physiological and/or morphological characteristics which are different from those of lettuce variety NUN 09093 LTL) or from a vegetatively propagated plant of variety NUN 09093 LTL (or from its progeny or from a plant having all but one, two or three physiological and/or morphological characteristics which are different from those of lettuce variety NUN 09093 LTL), wherein the plant part is a leaf, a harvested leaf, a part of a leaf, a head, a harvested head, a part of a head, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on lettuce variety NUN 09093 LTL, or a hypocotyl, a cotyledon, a pistil, an anther, or a flower or a part thereof.

Such plant part of lettuce variety NUN 09093 LTL can be stored and/or processed further. The disclosure thus also provides for a food or feed products comprising one or more of such parts, such as canned, chopped, cooked, roasted, in a sauce, in a sandwich, pasted, pureed or concentrated, juiced, frozen, dried, pickled, or powdered lettuce heads or leaves from lettuce variety NUN 09093 LTL or from progeny of said variety, or from a derived variety, such as a plant having all or all but one, two, or three of the physiological and/or morphological characteristics of lettuce variety NUN 09093 LTL. Preferably, the plant part is a lettuce head or leaf or a part thereof and/or an extract from a leaf or another plant part described herein comprising at least one cell of lettuce variety NUN 09093 LTL. The food or feed product may be fresh or processed, e.g., dried, grinded, powdered, pickled, chopped, cooked, roasted, in a sauce, in a sandwich, pasted, pureed or concentrated, juiced, pickled, canned, steamed, boiled, fried, blanched and/or frozen, etc.

In another aspect, the disclosure provides for a lettuce head or leaf of variety NUN 09093 LTL, or a part of a head or leaf of said variety. The head or leaf can be in any stage of maturity, for example, immature or mature.

In another aspect, the disclosure provides for a container comprising or consisting of a plurality of harvested lettuce heads or leaves or parts of lettuce heads or leaves of said variety, or lettuce heads or leaves of progeny thereof, or lettuce heads or leaves of a derived variety.

Marketable lettuce heads or leaves are generally sorted by size and quality after harvest. Alternatively, the lettuce heads or leaves can be sorted by leaf size, shape, texture, glossiness, or color.

Also, at-harvest and/or post-harvest characteristics of heads or leaves can be compared, such as cold storage holding quality, post-harvest leaf crispness and leaf browning or pinking after cutting can be measured using known methods.

In another aspect, the plant, plant part, or seed of lettuce variety NUN 09093 LTL is inside or more containers. For example, the disclosure provides containers such as cans, boxes, crates, bags, cartons, Modified Atmosphere Packaging Films (e.g., biodegradable films), etc. comprising a plant or part of a plant (fresh and/or processed) or seed of lettuce variety NUN 09093 LTL. In a particular aspect, the container comprises a plurality of seeds of lettuce variety NUN 09093 LTL, or a plurality of plant parts of lettuce variety NUN 09093 LTL. The seeds may be pelleted prior to packing (to form pills or pellets) and/or may be disinfected, primed and/or treated with various compounds, such as seed coating or crop protection compounds. The seed produces a plant of lettuce variety NUN 09093 LTL.

All documents (e.g., patent publications) are herein incorporated by reference in their entirety, including the following cited references:

Naktuinbow and NARO, "Calibration Manual: DUS Test for Lettuce," world-wide web at naktuinbow.nl US Department of Agriculture, Agricultural Marketing Service, "Objective Description of Variety—Lettuce (*Lactuca sativa* L.)", world wide web at ams.usda.gov/services/plant-variety-protection/pvpo-c-forms, under lettuce.

UPOV, "Guidelines for the Conduct of Tests for Distinctness, Uniformity and Stability", TG/13/11 (Geneva 2006, last updated 2017 Apr. 5), world-wide web at upov.int under edocs/tgdocs/en/tg013.pdf.

World Seed, Guidelines for the Handling of a Dispute on Essential Derivation in Lettuce Acquaah, G., "Principles of Plant Genetics and Breeding", Blackwell Publishing, 2007, ISBN-13: 978-1-4051-2646-4.

Bertier, L. D., et. al., "High-Resolution Analysis of the Efficiency, Heritability, and Editing Outcomes of CRISPR/Cas9-Induced Modifications of NCED4 in Lettuce (*Lactuca sativa*)," G3: Genes, Genomes, Genetics, 2018, vol. 8, pp. 1513-1521.

Brotman, Y., et. al., "Resistance Gene Homologues in Melon are Linked to Genetic Loci Conferring Disease and Pest Resistance", Theor Appl Genet, 2002, vol. 104, pp. 1055-1063, DOI 10.1007/s00122-001-0808-x Gonai, T., et al., "Abscisic Acid in the Thermoinhibition of Lettuce Seed Germination and Enhancement of its Catabolism by Gibberellin", Journal of Experimental Botany, 2004, vol. 55(394), pp. 111-118.

Hunter, P. J., et. al., "Oxidative Discolouration in Wholehead and Cut Lettuce: Biochemical and Environmental Influences on a Complex Phenotype and Potential Breeding Strategies to Improve Shelf-life," Euphytica, 2017, vol. 213(180), DOI 10.1007/s10681-017-1964-7.

Needleman, S. B., et. al., "A General Method Applicable to the Search for Similarities in the Amino Acid Sequence of Two Proteins", Journal of Molecular Biology, 1970, vol. 48(3), pp. 443-53.

Nikolova, V., et. al., "Diploidization of Cucumber (*Cucumis sativus* L.) Haploids by Colchini Treatment", Acta Societas Botanicorum Poloniae, 1996, vol. 65, pp. 311-317.

Smith, et. al., "Leaf Lettuce Production in California," 2011, University of California Agricultural and Natural Resources, Publication 7216, pp. 1-6.

Songstad, D. D., et. al., "Genome Editing of Plants," Critical Reviews in Plant Sciences, vol. 36, no. 1, pp 1-23.

Teng, W., et al., "Rapid Regeneration of Lettuce from Suspension Culture", HortScience, 1992, vol. 27(9), pp. 1030-1032.

Teng, W., et al., "Regenerating Lettuce from Suspension Culture in a 2-Liter Bioreactor", HortScience, 1993, vol. 28(6), pp. 669-671.

Turini, et. al., "Iceberg Lettuce Production in California," 2011, University of California Agricultural and Natural Resources, Publication 7215, pp. 1-6.

Vos, P., et al., "AFLP: A New Technique for DNA Fingerprinting", Nucleic Acids Research, 1995, vol. 23(21), pp. 4407-4414.

Wijnker, E., et al., "Hybrid Recreation by Reverse breeding in *Arabidopsis thaliana*", Nature Protocols, 2014, vol. 9, pp. 761-772. DOI: doi: 10.1038/nprot.2014.049

Zhang, X., et al., "Genotypic Effects on Tissue Culture Response of Lettuce Cotyledons", Journal of Genetics and Breeding, 1992, vol. 46, pp. 287-290.

US 2008/0222949

EP 1 197 137 A1

US 2015/0126380

WO 2017/144669

WO 2008/092505

U.S. Pat. No. 8,237,019

Development of Lettuce Variety NUN 09093 LTL

Lettuce variety NUN 09093 LTL was developed from an initial cross between lettuce lines. The female and male parents were crossed to produce seeds. After the cross, progeny was self-pollinated or backcrossed, followed by pedigree selection and line selection. Lettuce variety NUN 09093 LTL can be propagated by seeds or vegetatively, or by regeneration of a tissue culture. The seeds of lettuce variety NUN 09093 LTL can be grown to produce inbred plants and parts thereof (e.g., lettuce heads and leaves).

The Applicant concluded that lettuce variety NUN 09093 LTL is uniform and stable. This has been established through evaluation of horticultural characteristics. Several seed production events resulted in no observable deviation in genetic stability. Lettuce variety NUN 09093 LTL has been assigned an inventory ID of 107015076.

Deposit Information

A total of 2500 seeds of variety NUN 09093 LTL have been deposited and accepted according to the Budapest Treaty by Nunhems B.V. on Apr. 22, 2021 at the NCIMB Ltd., Ferguson Building, Craibstone Estate, Bucksburn, Aberdeen AB21 9YA, United Kingdom (NCIMB). The deposit has been assigned NCIMB 43767. A statement indicating the viability of the sample has been provided. A deposit of lettuce variety NUN 09093 LTL is also maintained at Nunhems B.V.

The deposit will be maintained in NCIMB for a period of 30 years, or 5 years after the most recent request, or for the enforceable life of the patent whichever is longer and will be replaced if it ever becomes nonviable during that period. Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. Applicant does not waive any rights granted under this patent on this application or under the Plant Variety Protection Act (7 U.S.C. § 2321 et seq.). Accordingly, the requirements of 37 CFR § 1.801-1.809 have been satisfied.

Characteristics of Lettuce Variety NUN 09093 LTL

The most similar variety to NUN 09093 LTL is referred to as NUN 09107, a variety from Nunhems B.V. with the commercial name Danstar.

In Tables 1 and 2, a comparison between lettuce variety NUN 09093 LTL and Reference Variety is shown based on a trial in the USA. Trial location: Acampo, Calif., USA; Seeding date: Jun. 1, 2020; Transplanting date: Jul. 2, 2020; Harvesting date: Jul. 27, 2020. In Table 3, the distinguishing characteristics between lettuce variety NUN 09093 LTL and the Reference Variety are shown.

One replication of 30 plants of each variety (i.e., application and reference varieties), from which at least 20 plants or plant parts were randomly selected and were used to measure characteristics. For numerical characteristics, averages were calculated. For non-numerical characteristics, the type/degree were determined. Similarity and differences between two different plant lines or varieties can be determined by comparing the number of morphological and/or physiological characteristics that are the same (i.e., statistically not significantly different) or that are different (i.e., statistically significantly different) between the two plant lines or varieties when grown under the same environmental conditions. A numerical characteristic is considered to be "the same" when the value for a numeric characteristic is not significantly different, e.g., at 5% (p<0.05) significance level, using T-test Paired Two Sample for Means, a standard method known to the skilled person. A non-numerical characteristic is considered to be "the same" when the values have the same "degree" or "type" when scored using USDA and/or UPOV descriptors, for plants are grown under the same environmental conditions. In one aspect, a statistical analysis of the quantitative characteristics showing the degree of significance at 5% significance level is provided (see, Tables 4-12).

In another aspect, the disclosure provides a lettuce plant having all of the physiological and morphological characteristics of lettuce variety NUN 09093 LTL as presented in Tables 1-2, when grown under the same environmental conditions.

TABLE 1

Characteristics of Lettuce Variety NUN 09093 LTL and the Reference Variety
(Exhibit C - USDA Descriptors) based on Holtville, California, USA

| Characteristics | Application Variety (NUN 09093 LTL) | Reference Variety (NUN 09107 LTL) |
|---|---|---|
| UPOV Morphology: | | |
| Seed: | | |
| Seed color:<br>white, yellow, brown, black | White | Black |
| Plant: | | |
| Degree of overlapping of upper part of leaves:<br>absent or weak, medium, strong | Absent or weak | Absent or weak |
| Number of leaves (only for varieties with degree of overlapping of upper part of leaves absent or weak):<br>very few, very few to few, few, few to medium, medium, medium to many, many, many to very many, very many | Few | Few to medium |
| Mature Leaf: | | |
| Leaf attitude:<br>erect, erect to semi-erect, semi-erect, semi-erect to horizontal, horizontal | Semi-erect | Semi-erect |
| Number of divisions:<br>absent or very few, very few to few, few, few to medium, medium, medium to many, many, many to very many, very many | Few | Very few to few |
| Longitudinal section:<br>concave, concave to flat, flat, flat to convex, convex | Concave | Flat |
| Anthocyanin coloration:<br>absent or very weak, very weak to weak, weak, weak to medium, medium, medium to strong, strong, strong to very strong, very strong | Absent or very weak | Absent or very weak |
| Color:<br>green, yellowish green, greyish green | Greyish green (RHS 138A) | Green (RHS 144A) |
| Intensity of green color:<br>very light, very light to light, light, light to medium, medium, medium to dark, dark, dark to very dark, very dark | Medium | Medium |
| Glossiness of upper side:<br>absent or very weak, very weak to weak, weak, weak to medium, medium, medium to strong, strong, strong to very strong, very strong | Medium | Medium |
| Thickness:<br>very thin, thin, medium, thick, very thick, | Thick | Thick |
| Blistering:<br>absent or very weak, very weak to weak, weak, weak to medium, medium, medium to strong, strong, strong to very strong, very strong | Absent or very weak | Absent or very weak |
| Size of blisters:<br>very small, very small to small, small, small to medium, medium, medium to large, large, large to very large, very large | Medium | Medium |
| Undulation of margin:<br>absent or very weak, very weak to weak, weak, weak to medium, medium, medium to strong, strong, strong to very strong, very strong | Medium | Strong |
| Type of incisions of margin:<br>crenate, regularly dentate, irregularly dentate, bidentate, tridentate | Bidentate | Bidentate |
| Depth of incisions of margin:<br>absent or very shallow, very shallow to shallow, shallow, shallow to medium, medium, medium to deep, deep, deep to very deep, very deep | Medium | Shallow to medium |
| Depth of secondary incisions of margin (only for varieties with type of incisions of margin irregularly dentate, bi- or tri-dentate):<br>very shallow, very shallow to shallow, shallow, shallow to medium, medium, medium to deep, deep, deep to very deep, very deep | Shallow to medium | Shallow |

TABLE 1-continued

Characteristics of Lettuce Variety NUN 09093 LTL and the Reference Variety
(Exhibit C - USDA Descriptors) based on Holtville, California, USA

| Characteristics | Application Variety (NUN 09093 LTL) | Reference Variety (NUN 09107 LTL) |
|---|---|---|
| Density of incisions of margin: very sparse, very sparse to sparse, sparse, sparse to medium, medium, medium to dense, dense, dense to very dense, very dense | Medium | Medium |
| Venation: not flabellate, semi-flabellate, flabellate | Flabellate | Semi-flabellate |
| Resistance: absent or present | | |
| Resistance to *Bremia lactucae* Isolate B1: 16 EU | Present | Present |
| Resistance to *Bremia lactucae* Isolate B1: 17 EU | Present | Present |
| Resistance to *Bremia lactucae* Isolate B1: 18 EU | Present | Present |
| Resistance to *Bremia lactucae* Isolate B1: 20 EU | Present | Present |
| Resistance to *Bremia lactucae* Isolate B1: 21 EU | Present | Present |
| Resistance to *Bremia lactucae* Isolate B1: 22 EU | Present | Present |
| Resistance to *Bremia lactucae* Isolate B1: 23 EU | Present | Present |
| Resistance to *Bremia lactucae* Isolate B1: 24 EU | Present | Present |
| Resistance to *Bremia lactucae* Isolate B1: 25 EU | Present | Present |
| Resistance to *Bremia lactucae* Isolate B1: 26 EU | Present | Present |
| Resistance to *Bremia lactucae* Isolate B1: 27 EU | Present | Present |
| Resistance to *Bremia lactucae* Isolate B1: 28 EU | Present | Present |
| Resistance to *Bremia lactucae* Isolate B1: 29 EU | Present | Present |
| Resistance to *Bremia lactucae* Isolate B1: 30 EU | Present | Present |
| Resistance to *Bremia lactucae* Isolate B1: 31 EU | Present | Present |
| Resistance to *Bremia lactucae* Isolate B1: 32 EU | Present | Present |
| Resistance to *Bremia lactucae* Isolate B1: 33 EU | Present | Present |
| Resistance to *Bremia lactucae* Isolate B1: 34 EU | Absent | Present |
| Resistance to *Bremia lactucae* Isolate B1: 35 EU | Absent | Present |
| Resistance to *Bremia lactucae* Isolate B1: 36 EU | Absent | Present |
| Resistance to *Nasonovia ribisnigri* (Nr) Biotype Nr: 0 | Present | Present |
| Resistance to *Fusarium oxysporum* sp. *lactucae* Race Fol: 1 | Intermediate Resistant | Intermediate Resistant |
| Resistance to Lettuce Mosaic Virus (LMV) Pathotype II | Absent | Absent |
| Resistance to Lettuce Root Aphids | Absent | Absent |
| Resistance to *Rhizomonas subefaciens* (Corky Root) | Absent | Absent |
| Bolting: | | |
| Time of beginning of bolting: very early, very early to early, early, early to medium, medium, medium to late, late, late to very late | Very slow | Very slow |
| USDA Morphology: | | |
| Plant type: | | |
| Butterhead, Novita Type, Iceberg Type, Batavia Type, Frisee d'Amerique Type, Lollo Type, Oakloaf Type, Multi-divided Type, Frillice Type, Cos or Romaine, Bibb/Gem, Stem, Cutting/Whole Leaf, Latin, Other (specify) | Frillice | Frillice |
| Spread of frame leaves, cm: | 21.14 cm | 25.44 cm |
| Cotyledon to 4$^{th}$ leaf stage: | | |
| Shape of cotyledon: broad, intermediate, spatulate | Broad | Broad |
| Shape of fourth leaf: transverse oval, round, oval, elongated, lanceolate, pinnately lobed | Elongated | Elongated |
| Butt: | | |
| Shape: slightly concave, flat, rounded | Flat | Flat |
| Midrib: flattened, moderately raised, prominently raised | Moderately raised | Moderately raised |

TABLE 2

Characteristics of Lettuce Variety NUN 09093 LTL and the Reference Variety (Non-USDA Descriptors) based on Acampo, California, USA Trial

| Characteristics | Application Variety (NUN 09093 LTL) | Reference Variety (NUN 09107 LTL) |
|---|---|---|
| Cotyledon to fourth leaf stage: | | |
| Length of fourth leaf, mm: | 82.10 mm | 69.97 mm |
| Width of fourth leaf, mm: | 18.82 mm | 24.09 mm |
| Apical margin: entire, crenate, finely dentate, moderately dentate, coarsely dentate, incised, lobed | Dentate | Coarsely dentate |
| Basal margin: entire, crenate, finely dentate, moderately dentate, coarsely dentate, incised, lobed | Dentate | Dentate |
| Undulation: flat, slight, medium, marked | Slight | Slight |
| Color: | Moderate yellow green (RHS 146C) | Strong yellow green (RHS 144A) |
| Cupping: uncapped, slight, markedly | Slight | Slight |
| Reflexing: none, apical margin, lateral margin | None | None |
| Leaf attitude (at 10-12 leaf stage): erect, semi-erect, prostate | Semi-erect | Semi-erect |
| Leaf blade division (at 10-12 leaf stage): entire, lobed, divided | Divided | Divided |
| Mature leaves (harvest mature outer leaves): | | |
| Length, mm: | 120.55 mm | 140.60 mm |
| Width, mm: | 132.58 mm | 160.87 mm |
| Size: small, medium, large | Small | Medium |
| Trichomes: absent, present | Present | Present |
| Axillary sprouting: absent or very weak, weak, medium, strong, very strong | Absent or very weak | Absent or very weak |
| Incision of margin on apical part: absent, present | Present | Present |
| Plant: | | |
| Height, cm: | 8.89 cm | 11.01 cm |
| Weight, g: | 93.60 g | 125.20 g |
| Diameter: very small, small, medium, large, very large | Small | Medium |
| Head formation: no head, open head, closed head | No head | No head |
| Core: | | |
| Diameter at base of head, mm (core width): | 10.71 mm | 14.17 mm |
| Height from base of head to apex (mm), average (core length): | 12.68 mm | 17.52 mm |
| Height from base of head to apex (mm), range (min-max): | 10.09-15.01 mm | 15.04-20.50 mm |

TABLE 3

Distinguishing Characteristics between Lettuce Variety NUN 09093 LTL and the Reference Variety

| Characteristics | Application Variety (NUN 09093 LTL) | Reference Variety (NUN 09107 LTL) |
|---|---|---|
| Seed: | | |
| Seed color: white, yellow, brown, black | White | Black |
| Plant: | | |
| Number of leaves (only for varieties with degree of overlapping of upper part of leaves absent or weak): very few, very few to few, few, few to medium, medium, medium to many, many, many to very many, very many | Few | Few to medium |

TABLE 3-continued

Distinguishing Characteristics between Lettuce
Variety NUN 09093 LTL and the Reference Variety

| Characteristics | Application Variety (NUN 09093 LTL) | Reference Variety (NUN 09107 LTL) |
|---|---|---|
| Spread of frame leaves, cm: | 21.14 cm | 25.44 cm |
| Height, cm: | 8.89 cm | 11.01 cm |
| Weight, g: | 93.60 g | 125.20 g |
| Diameter: very small, small, medium, large, very large | Small | Medium |
| Cotyledon to fourth leaf stage: | | |
| Length of fourth leaf, mm: | 82.10 mm | 69.97 mm |
| Width of fourth leaf, mm: | 18.82 mm | 24.09 mm |
| Apical margin: entire, crenate, finely dentate, moderately dentate, coarsely dentate, incised, lobed | Dentate | Coarsely dentate |
| Color: | Moderate yellow green (RHS 146C) | Strong yellow green (RHS 144A) |
| Mature leaf: | | |
| Number of divisions: absent or very few, very few to few, few, few to medium, medium, medium to many, many, many to very many, very many | Few | Very few to few |
| Longitudinal section: concave, concave to flat, flat, flat to convex, convex | Concave | Flat |
| Color: green, yellowish green, greyish green | Greyish green (RHS 138A) | Green (RHS 144A) |
| Undulation of margin: absent or very weak, very weak to weak, weak, weak to medium, medium, medium to strong, strong, strong to very strong, very strong | Medium | Strong |
| Depth of incisions of margin: absent or very shallow, very shallow to shallow, shallow, shallow to medium, medium, medium to deep, deep, deep to very deep, very deep | Medium | Shallow to medium |
| Depth of secondary incisions of margin (only for varieties with type of incisions of margin irregularly dentate, bi- or tri-dentate): very shallow, very shallow to shallow, shallow, shallow to medium, medium, medium to deep, deep, deep to very deep, very deep | Shallow to medium | Shallow |
| Venation: not flabellate, semi-flabellate, flabellate | Flabellate | Semi-flabellate |
| Length, mm: | 120.55 mm | 140.60 mm |
| Width, mm: | 132.58 mm | 160.87 mm |
| Size: small, medium, large | Small | Medium |
| Core: | | |
| Diameter at base of head, mm (core width): | 10.71 mm | 14.17 mm |
| Height from base of head to apex (mm), average (core length): | 12.68 mm | 17.52 mm |

The results of the T-Test Paired Sample Means show significant differences at 5% significance level between lettuce variety NUN 09093 LTL and the Reference Variety for fourth leaf length, fourth leaf width, plant spread of frame leaves, plant height, plant weight, mature leaf length, mature leaf width, height from base of head to apex (core length), and diameter at base of head (core width) as shown in Tables 4-12.

Table 4 shows a significant difference between lettuce variety NUN 09093 LTL and the Reference Variety ($p<0.001$) for fourth leaf length (mm) based on the results of the trial conducted in the US during the trial season 2020.

TABLE 4

| Statistical Parameter | Application Variety (NUN 09093 LTL) | Reference Variety (NUN 09107 LTL) |
|---|---|---|
| Number of samples | 20 | 20 |
| Min. | 69.47 | 54.72 |
| Max | 99.42 | 88.85 |
| Median | 80.90 | 68.45 |
| Mean | 82.10 | 69.67 |
| Standard deviation | 5.75 | 9.63 |

Table 5 shows a significant difference between lettuce variety NUN 09093 LTL and the Reference Variety ($p<0.001$) for fourth leaf width (mm) based on the results of the trial conducted in the US during the trial season 2020.

TABLE 5

| Statistical Parameter | Application Variety (NUN 09093 LTL) | Reference Variety (NUN 09107 LTL) |
|---|---|---|
| Number of samples | 20 | 20 |
| Min. | 14.15 | 17.23 |
| Max | 23.65 | 31.58 |
| Median | 19.0 | 24.23 |
| Mean | 18.82 | 24.09 |
| Standard deviation | 2.66 | 4.10 |

Table 6 shows a significant difference between lettuce variety NUN 09093 LTL and the Reference Variety ($p<0.001$) for plant spread of frame leaves (cm) based on the results of the trial conducted in the US during the trial season 2020.

TABLE 6

| Statistical Parameter | Application Variety (NUN 09093 LTL) | Reference Variety (NUN 09107 LTL) |
|---|---|---|
| Number of samples | 20 | 20 |
| Min. | 17.10 | 19.0 |
| Max | 25.30 | 29.80 |
| Median | 21.15 | 25.35 |
| Mean | 21.14 | 25.44 |
| Standard deviation | 1.61 | 2.40 |

Table 7 shows a significant difference between lettuce variety NUN 09093 LTL and the Reference Variety ($p<0.001$) for plant height (cm) based on the results of the trial conducted in the US during the trial season 2020.

TABLE 7

| Statistical Parameter | Application Variety (NUN 09093 LTL) | Reference Variety (NUN 09107 LTL) |
|---|---|---|
| Number of samples | 20 | 20 |
| Min. | 7.30 | 8.90 |
| Max | 10.60 | 14.30 |
| Median | 8.80 | 10.75 |
| Mean | 8.89 | 11.01 |
| Standard deviation | 0.95 | 1.53 |

Table 8 shows a significant difference between lettuce variety NUN 09093 LTL and the Reference Variety ($p=0.001$) for plant weight (g) based on the results of the trial conducted in the US during the trial season 2020.

TABLE 8

| Statistical Parameter | Application Variety (NUN 09093 LTL) | Reference Variety (NUN 09107 LTL) |
|---|---|---|
| Number of samples | 20 | 20 |
| Min. | 58.0 | 78.0 |
| Max | 162.0 | 196.0 |
| Median | 90.0 | 128.0 |
| Mean | 93.60 | 125.20 |
| Standard deviation | 26.11 | 31.33 |

Table 9 shows a significant difference between lettuce variety NUN 09093 LTL and the Reference Variety ($p<0.001$) for mature leaf length (mm) based on the results of the trial conducted in the US during the trial season 2020.

TABLE 9

| Statistical Parameter | Application Variety (NUN 09093 LTL) | Reference Variety (NUN 09107 LTL) |
|---|---|---|
| Number of samples | 20 | 20 |
| Min. | 108.92 | 128.44 |
| Max | 129.93 | 157.06 |
| Median | 119.91 | 139.23 |
| Mean | 120.55 | 140.60 |
| Standard deviation | 5.43 | 8.55 |

Table 10 shows a significant difference between lettuce variety NUN 09093 LTL and the Reference Variety ($p<0.001$) for mature leaf width (mm) based on the results of the trial conducted in the US during the trial season 2020.

TABLE 10

| Statistical Parameter | Application Variety (NUN 09093 LTL) | Reference Variety (NUN 09107 LTL) |
|---|---|---|
| Number of samples | 20 | 20 |
| Min. | 115.87 | 146.51 |
| Max | 147.17 | 176.60 |
| Median | 133.65 | 160.14 |
| Mean | 132.58 | 160.87 |
| Standard deviation | 8.61 | 8.08 |

Table 11 shows a significant difference between lettuce variety NUN 09093 LTL and the Reference Variety ($p<0.001$) for height from base of head to apex (core length, mm) based on the results of the trial conducted in the US during the trial season 2020.

TABLE 11

| Statistical Parameter | Application Variety (NUN 09093 LTL) | Reference Variety (NUN 09107 LTL) |
|---|---|---|
| Number of samples | 20 | 20 |
| Min. | 10.09 | 15.04 |
| Max | 15.01 | 20.50 |
| Median | 12.29 | 17.57 |
| Mean | 12.68 | 17.52 |
| Standard deviation | 1.46 | 1.58 |

Table 12 shows a significant difference between lettuce variety NUN 09093 LTL and the Reference Variety ($p<0.001$) for diameter at base of head (core width, mm) based on the results of the trial conducted in the US during the trial season 2020.

TABLE 12

| Statistical Parameter | Application Variety (NUN 09093 LTL) | Reference Variety (NUN 09107 LTL) |
|---|---|---|
| Number of samples | 20 | 20 |
| Min. | 9.14 | 12.92 |
| Max | 11.91 | 15.82 |
| Median | 10.64 | 13.95 |
| Mean | 10.71 | 14.17 |
| Standard deviation | 0.88 | 0.94 |

The invention claimed is:

1. A plant, plant part, or seed of lettuce variety NUN 09093 LTL, wherein a representative sample of seed of said variety has been deposited under Accession Number NCIMB 43767.

2. The plant part of claim 1, wherein the plant part is a head, a leaf, pollen, an ovule, a fruit, a scion, a rootstock, a cutting, a flower, or a cell.

3. A seed that produces the plant of claim 1.

4. A seed grown on the plant of claim 1.

5. A lettuce plant or a part thereof having all the physiological and morphological characteristics of the plant of claim 1, when grown under the same environmental conditions.

6. A tissue or cell culture of regenerable cells of the plant or plant part of claim 1.

7. The tissue or cell culture according to claim 6, comprising cells or protoplasts derived from a plant part suitable for vegetative reproduction, wherein the plant part is an embryo, a meristem, a cotyledon, a hypocotyl, a pollen, a leaf, an anther, a root, a root tip, a pistil, a petiole, a flower, a fruit, a seed, a stem, or a stalk.

8. A lettuce plant regenerated from the tissue or cell culture of claim 6, wherein the plant has all of the physiological and morphological characteristics of the plant of lettuce variety NUN 09093 LTL, when the numerical characteristics are determined at 5% significance level and determined by type or degree for non-numerical characteristics, when grown under the same environmental conditions, and wherein a representative sample of seed of said lettuce variety has been deposited under Accession Number NCIMB 43767.

9. A method of producing of the plant of claim 1, said method comprising vegetative propagation of at least a part of the plant of lettuce variety NUN 09093 LTL, wherein a representative sample of seed of said lettuce variety has been deposited under Accession Number NCIMB 43767.

10. The method of claim 9, wherein said vegetative propagation comprises regenerating a whole plant from a part of lettuce variety NUN 09093 LTL, wherein a representative sample of seed of said lettuce variety has been deposited under Accession Number NCIMB 43767.

11. The method of claim 9, wherein said part is a cutting, a cell culture, or a tissue culture.

12. A plant vegetatively propagated from the plant of claim 1, or part thereof, wherein the vegetatively propagated plant, or part thereof have all of the physiological and morphological characteristics of the plant of lettuce variety NUN 09093 LTL, when the numerical characteristics are determined at 5% significance level and determined by type or degree for non-numerical characteristics, when grown under the same environmental conditions, and wherein a representative sample of seed of said lettuce variety has been deposited under Accession Number NCIMB 43767.

13. A method of producing a lettuce plant, said method comprising crossing the plant of claim 1 with itself or a second lettuce plant, selecting a progeny lettuce plant from said crossing, allowing the progeny lettuce plant to form seed, and optionally repeating the crossing and selecting one or more times to produce further progeny seed.

14. A first generation progeny of the lettuce plant of claim 1, obtained by crossing the plant of lettuce variety NUN 09093 LTL with itself or another lettuce plant, wherein the progeny lettuce plant has all of the physiological and morphological characteristics of the plant of lettuce variety NUN 09093 LTL, and wherein a representative sample of seed of said lettuce variety has been deposited under Accession Number NCIMB 43767.

15. A method of producing an F1 hybrid lettuce seed, said method comprising crossing a first parent lettuce plant with a second parent lettuce plant and harvesting the resultant hybrid lettuce seed, wherein at the first parent lettuce plant or second parent lettuce plant is the plant of claim 1.

16. An F1 hybrid lettuce seed produced by the method of claim 15.

17. An F1 hybrid lettuce plant or part thereof, produced by growing the seed of claim 16.

18. A food, a feed, or a processed product comprising the plant part of claim 2.

19. A container comprising the plant, plant part, or seed of claim 1.

20. A method of introducing a desired trait into the plant of claim 1, said method comprises transforming the plant of lettuce variety NUN 09093 LTL with a transgene that confers the desired trait, wherein a representative sample of seed of said lettuce variety has been deposited under Accession Number NCIMB 43767, and wherein the desired trait is yield, storage properties, color, enhanced nutritional quality, male sterility, herbicide tolerance, insect resistance, pest resistance, disease resistance, environmental stress tolerance, modified carbohydrate metabolism, or modified protein metabolism.

21. A lettuce plant produced by the method of claim 20, wherein the transformed plant contains the desired trait and otherwise retains all of the morphological and physiological characteristics of the plant of lettuce variety NUN 09093 LTL.

22. A method of introducing a single locus conversion into the plant of claim 1 comprising:
   a. crossing the plant of claim 1 with a second lettuce plant comprising a desired single locus to produce F1 progeny plants;
   b. selecting F1 progeny plants that have the single locus to produce selected F1 progeny plants;
   c. crossing the selected F1 progeny plants with lettuce variety NUN 09093 LTL to produce backcross progeny plants;
   d. selecting backcross progeny plants that have the single locus and otherwise comprise all of the physiological and morphological characteristics of lettuce variety NUN 09093 LTL to produce selected backcross progeny plants; and
   e. repeating steps (c) and (d) one or more times in succession to produce selected second or higher backcross progeny plants that comprise the single locus and otherwise comprise all of the physiological and morphological characteristics of the plant of lettuce variety NUN 09093 LTL, wherein a representative sample of seed of said lettuce variety has been deposited under Accession Number NCIMB 43767.

23. The method of claim 22, wherein the single locus confers yield, storage properties, color, enhanced nutritional quality, male sterility, herbicide tolerance, insect resistance, pest resistance, disease resistance, environmental stress tolerance, modified carbohydrate metabolism, or modified protein metabolism.

24. A lettuce plant produced by the method of claim 22, wherein the single locus converted plant comprises the single locus conversion and otherwise has all of the morphological and physiological characteristics of the plant of lettuce variety NUN 09093 LTL.

25. A method of producing a modified lettuce plant, said method comprising mutating a target gene in lettuce plant or plant part of lettuce variety NUN 09093 LTL, wherein a representative sample of seed of said lettuce variety has been deposited under Accession Number NCIMB 43767.

26. The method of claim 25, wherein the target gene modifies a desired trait and wherein the desired trait is yield, storage properties, color, male sterility, herbicide tolerance, insect resistance, pest resistance, disease resistance, environmental stress tolerance, modified carbohydrate metabolism, or modified protein metabolism or the mutation occurs in any of the following genes: Ferulate-5-hydroxylase, dmr1, dmr6, NCED4, PAL, PPO.

27. The method of claim 25, wherein the target gene is mutated by targeted gene editing.

28. A lettuce plant produced by the method of claim 25, wherein the modified lettuce plant contains the desired trait and otherwise has all of the physiological and morphological characteristics of lettuce variety NUN 09093 LTL.

29. A method of producing doubled haploid cells of the plant of claim 1, said method comprising making doubled haploid cells from haploid cells from the plant or seed of lettuce variety NUN 09093 LTL, wherein a representative sample of seed of said lettuce variety has been deposited under Accession Number NCIMB 43767.

30. A method for determining the genotype of the plant of claim 1, said method comprising obtaining a sample of nucleic acids from said plant and detecting in said nucleic acids a plurality of polymorphisms, thereby determining the genotype of the plant and storing the results of detecting the plurality of polymorphisms on a computer readable medium.

31. A method of producing a lettuce head or a lettuce leaf, said method comprising growing the plant of claim 1 until it develops at least a leaf or head, and collecting the leaf or head.

32. A lettuce head or a lettuce leaf produced by the method of claim 31.

33. A lettuce plant or part thereof which does not differ from the plant of claim 1 when the numerical characteristics are determined at 5% significance level and determined by type or degree for non-numerical characteristics, when grown under the same environmental conditions, and wherein a representative sample of seeds of said lettuce variety NUN 09093 LTL has been deposited under Accession Number NCIMB 43767.

34. A method for developing a lettuce plant in a lettuce breeding program, said method comprising applying plant breeding techniques comprising recurrent selection, backcrossing, pedigree breeding, mass selection, mutation breeding, genetic marker enhanced selection, or genetic transformation to the plant of claim 1 or part thereof, wherein said plant breeding techniques result in a development of a lettuce plant.

35. A method of producing a lettuce plant derived from the plant of claim 1 comprising:
 a. preparing a progeny lettuce plant derived from lettuce variety NUN 09093 LTL by crossing the plant of claim 1 with itself or with a second lettuce plant, wherein a representative sample of seed of said lettuce variety has been deposited under Accession Number NCIMB 43767;
 b. crossing the progeny plant with itself or a second lettuce plant to produce seed of a progeny plant of a subsequent generation;
 c. growing a progeny plant of a subsequent generation from said seed and crossing the progeny plant of a subsequent generation with itself or a second lettuce plant; and
 d. repeating step (b) and/or (c) for at least one more generation to produce a lettuce plant derived from lettuce variety NUN 09093 LTL.

* * * * *